(12) United States Patent
Lill et al.

(10) Patent No.: US 10,597,417 B2
(45) Date of Patent: Mar. 24, 2020

(54) PROCESSES FOR THE PREPARATION OF GALNAC ACID DERIVATIVES

(71) Applicant: Hoffmann-La Roche Inc., Little Falls, NJ (US)

(72) Inventors: Joerg Lill, Aarau (CH); Rene Trussardi, Birsfelden (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/890,181

(22) Filed: Feb. 6, 2018

(65) Prior Publication Data
US 2018/0162894 A1    Jun. 14, 2018

Related U.S. Application Data

(63) Continuation of application No. PCT/EP2016/068361, filed on Aug. 2, 2016.

(30) Foreign Application Priority Data

Aug. 6, 2015 (EP) .................. 15180058

(51) Int. Cl.
| | | |
|---|---|---|
| *C07H 15/08* | (2006.01) | |
| *C07H 1/00* | (2006.01) | |
| *C07H 21/02* | (2006.01) | |
| *A61K 47/54* | (2017.01) | |
| *C07C 269/06* | (2006.01) | |
| *C07C 271/22* | (2006.01) | |
| *C07C 245/20* | (2006.01) | |
| *C07C 67/11* | (2006.01) | |
| *C07C 51/41* | (2006.01) | |
| *C07C 229/26* | (2006.01) | |

(52) U.S. Cl.
CPC .......... *C07H 15/08* (2013.01); *A61K 47/549* (2017.08); *C07C 51/41* (2013.01); *C07C 67/11* (2013.01); *C07C 229/26* (2013.01); *C07C 245/20* (2013.01); *C07C 269/06* (2013.01); *C07C 271/22* (2013.01); *C07H 1/00* (2013.01); *C07H 21/02* (2013.01); *C07C 2603/18* (2017.05)

(58) Field of Classification Search
None
See application file for complete search history.

(56) References Cited

U.S. PATENT DOCUMENTS

2011/0207799 A1* 8/2011 Rozema .................. A61K 9/08
                                                        514/44 A

FOREIGN PATENT DOCUMENTS

| WO | 2010/108125 A2 | 9/2010 |
|----|----------------|--------|
| WO | 2011/104169    | 9/2011 |
| WO | 2012/083046 A2 | 6/2012 |
| WO | 2012/083185 A2 | 6/2012 |
| WO | 2014/179620 A1 | 11/2014 |
| WO | 2014/207232 A1 | 12/2014 |
| WO | 2015/071388 A1 | 5/2015 |
| WO | 2015/168589 A2 | 11/2015 |

OTHER PUBLICATIONS

CAS Registry entry for Registry No. 156917-23-9, Aug. 10, 1994.*
CAS Registry entry for Registry No. 133170-57-7, Apr. 12, 1991.*
CAS Registry entry for Registry No. 1185198-47-3, Sep. 16, 2009.*
Chakravarty et al., "Plasmin-Activated Prodrugs for Cancer Chemotherapy. 2. Synthesis and Biological Activity of Peptidyl Derivatives of Doxorubicin" Journal of Medicinal Chemistry 26(5):638-644 (Jan. 1, 1983).

(Continued)

*Primary Examiner* — Layla D Berry
(74) *Attorney, Agent, or Firm* — Todd M. Crissey

(57) ABSTRACT

The invention comprises a new process for the preparation of GalNAc derivatives of the formula I

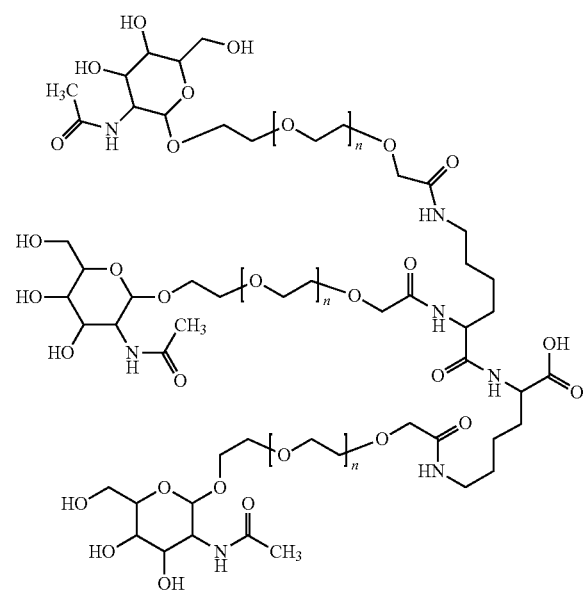

wherein n is an integer between 0 and 10 and its salts, corresponding enantiomers and/or optical isomers thereof. The GalNAc acid derivative of formula I can be used for the preparation of therapeutically valuable GalNAc oligonucleotide conjugates.

29 Claims, No Drawings

(56) References Cited

OTHER PUBLICATIONS

De Nitecki et al., "The Synthesis of the Pentapeptide Related to the gm(a) Antigen of human gamma G-Globulin" Australian Journal of Chemistry 22(4):841-847 (Jan. 1, 1969).

Iselin et al., "Derivate von L-Methionin-sulfoxyd und ihre Verwendung für Peptidsynthesen" Helvetica Chimica ACTA 44(1):61-78 (Oct. 24, 1961).

ISR and Written Opinion of PCT/EP2016/068361 (dated Sep. 19, 2016).

Kessler and Iselin, "Selektive Spaltung substituierter Phenylsulfenyl-Schutzgruppen bei Peptidsynthesen" Helvetica Chimica ACTA 49(4):1330-1334 (Jan. 1, 1966).

Schiesser et al., "Synthesis and DNA-Damaging Properties of Cisplatin-N-Mustard Conjugates" European Journal of Organic Chemistry 2015(12):2654-2660 (Apr. 13, 2015).

Zhao et al., "N-(2-Chloro-9H-purin-6-yl)-N-cyclopropylcylamino acids and derivatives Synthesis,evaluation as a class of novel analgesics, and 3D QSAR analysis" Bioorganic & Medicinal Chemistry 17:6305-6310 (Sep. 1, 2009).

ISR of PCT/EP2016/077516, dated Jan. 20, 2017.

MacMillian et al., "Evaluation of alternative solvents in common amide coupling reactions: replacement of dichloromethane and N,N-dimethylformamide" Green Chemistry 15:596-600 (2013).

Maruzen et al., "Synthesis of Organic Compounds IV-Carboxylic Acid" The Chemical Society of Japan 5th Edition:121-123 (2005).

Thazha P. Prakash et al., "Solid-phase synthesis of 50-triantennary N-acetylgalactosamine conjugated antisense oligonucleotides using phosphoramidite chemistry" Bioorganic & Medicinal Chemistry Letters 25(19):4127-4130 (Aug 8, 2015).

\* cited by examiner

PROCESSES FOR THE PREPARATION OF GALNAC ACID DERIVATIVES

CROSS REFERENCE TO RELATED APPLICATIONS

This application is a continuation of PCT/EP2016/068361, filed 2 Aug. 2016, which claims priority to European Patent Application No. 15180058.8, filed 6 Aug. 2015, the contents of which are incorporated by reference in their entireties.

The invention relates to a new process for the preparation of GalNAc derivatives of the formula I

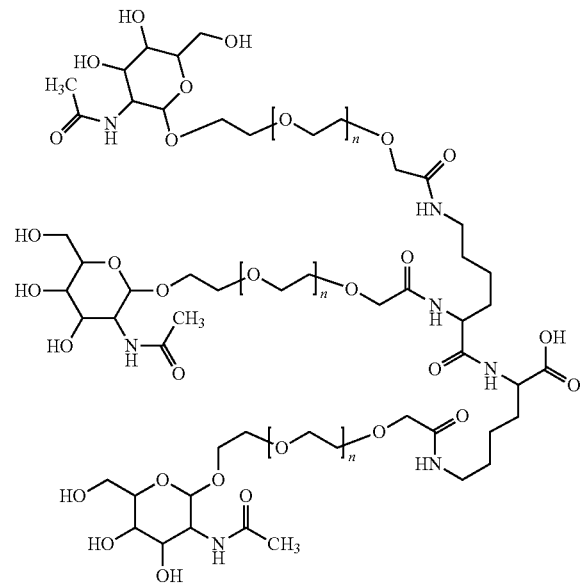

wherein n is an integer between 0 and 10 and its salts, corresponding enantiomers and/or optical isomers thereof.

GalNAc derivatives of formula I are usually the targeting moiety of conjugates comprising the GalNAc moiety and certain oligonucleotides. The GalNAc moiety due to its affinity to the asialoglycoprotein receptor which is located on the liver cell enables functional delivery of oligonucleotide conjugates to the liver cell. Such GalNAc cluster antisense conjugates have the potential to act as pharmacokinetic modulators and are e.g. described in the PCT Publication WO 2012/083046 or in the US Patent Application Publication US 2011/0207799. While these publications also disclose processes for the preparation of the GalNAc derivatives it was found that these processes do not meet the standard for a technical scale synthesis.

Object of the invention therefore is to provide an improved method for the preparation of the GalNAc derivatives of formula I which meets the requirements of an industrial scale process.

Further object of the invention is the use of the GalNAc acid derivative of formula I for the preparation of therapeutically valuable GalNAc oligonucleotide conjugates and of a process for the preparation of such conjugates.

The object could be achieved with the process of the present invention which comprises a) the coupling of a triamine salt of formula II

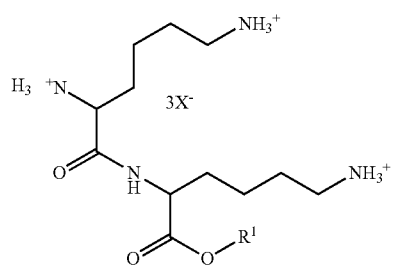

wherein $R^1$ is an ester protecting group and X is an anion of an acid with a tetrahydropyran acid of formula III

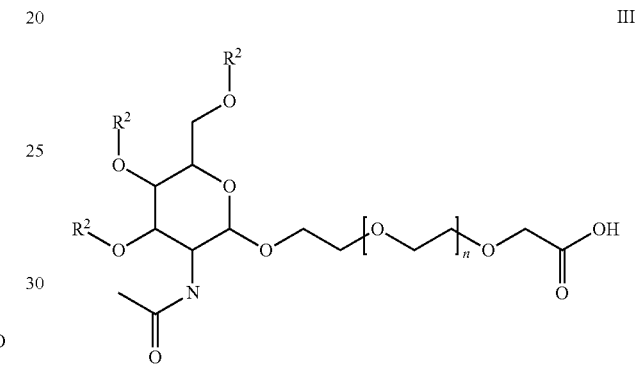

wherein n is as above and $R^2$ is a hydroxy protecting group in the presence of a peptide coupling agent, an amine base and an organic solvent to form the GalNAc ester of formula IV

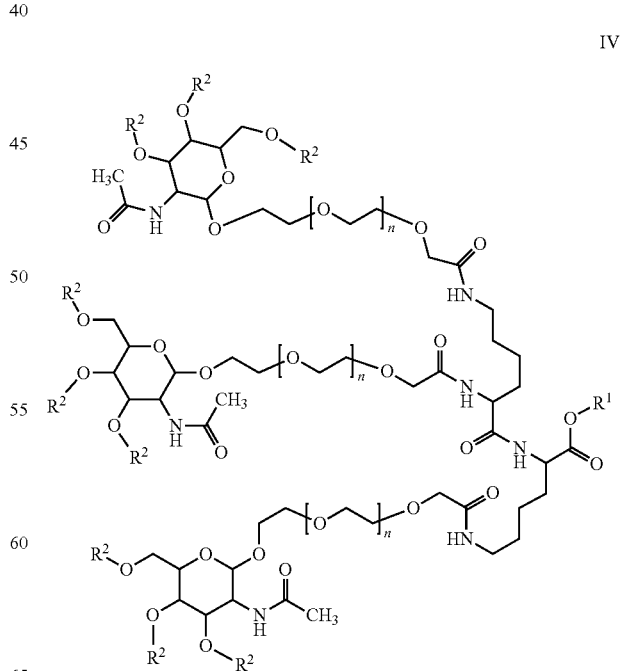

wherein n, $R^1$ and $R^2$ are as above;

b) the removal of the ester protecting group $R^1$ and of the hydroxy protecting groups $R^2$ in the presence of a mineral base to form the GalNAc acid salt of formula V c)

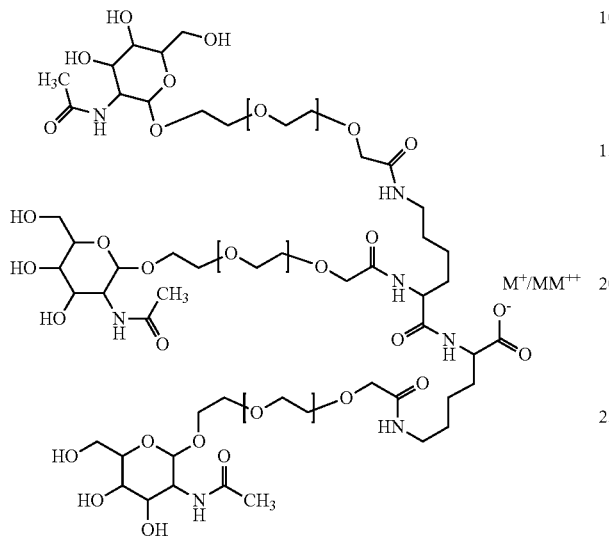

V wherein n is as above and M is a metal kation;
and c) optionally the transformation of the GalNAc acid salt of formula V into the GalNAc acid derivative of formula I.

The following definitions are set forth to illustrate and define the meaning and scope of the various terms used to describe the invention herein.

Whenever a chiral carbon is present in a chemical structure, it is intended that all stereoisomers associated with that chiral carbon are encompassed by the structure as pure stereoisomers as well as mixtures thereof.

The term "$C_{1-7}$ alkyl" denotes a monovalent linear or branched saturated hydrocarbon group of 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term phenyl-$C_{1-7}$-alkyl denotes a phenyl group which is attached to a $C_{1-7}$ alkyl group as defined above. A particular example is the benzyl group.

The phenyl group can optionally be substituted with halogen such as chlorine, bromine or iodine or with a $C_{1-7}$-alkyl group as defined above.

The term "amino-protecting group" denotes groups intended to protect an amino group and includes benzyl, benzyloxycarbonyl, carbobenzyloxy (CBZ or Z), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. Preferred amino protecting groups are FMOC and BOC.

The term "hydroxy-protecting group" and the term "ester protecting group" denote groups which intended to protect a hydroxy group and include ester- and ether-forming groups, in particular tetrahydropyranyl, benzoyl, acetyl, carbamoyl, benzyl and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981.

In a preferred embodiment the GalNAc derivative has the formula Ia wherein n is as above.

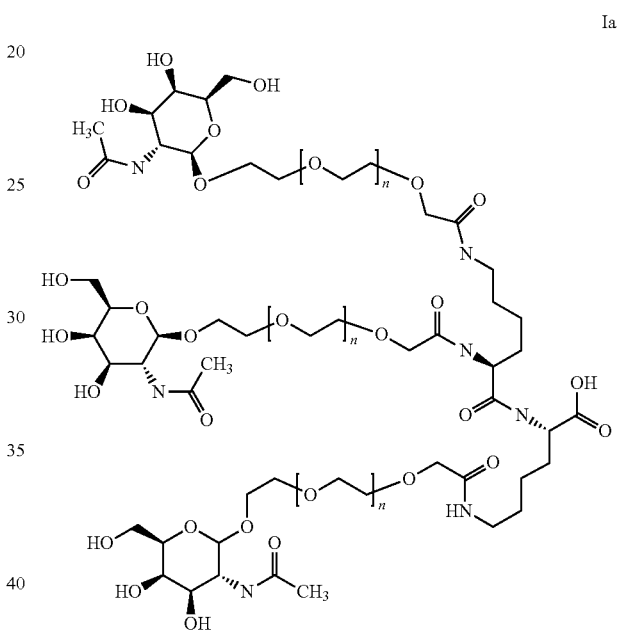

Ia

Likewise in accordance with formula Ia the intermediates II, III, IV, X, XI, XII, XIII, XIV, XX, XXI and XXII share the same stereochemistry at its chiral centers.

Synthesis of the Triamine Salt of Formula II (Building Block A):

The process comprises a1) transforming the carboxylic acid of formula X

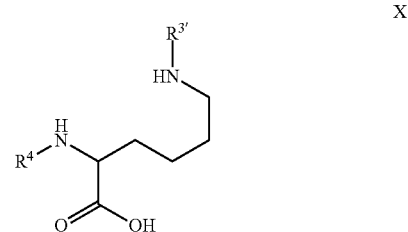

X wherein $R^{3'}$ and $R^4$ are different and independent of each other are an amino protecting group into an ester of formula XI

XI

[structure: R³'-HN-CH₂CH₂CH₂-CH(NHR⁴)-C(=O)-O-R¹]

wherein R¹ is an ester protecting group and R³' and R⁴ are as above;

b1) removing the amino protecting group R⁴ and subsequent forming of an amine salt of formula XII

XII

[structure: X⁻, R³'-HN-CH₂CH₂CH₂-CH(N⁺H₃)-C(=O)-O-R¹]

wherein R¹ and R³' are as above and X⁻ is an acid anion;

c1) coupling the amine salt of formula XII with a hexanoic acid derivative of formula XIII

XIII

[structure: R³''''-NH-CH₂CH₂CH₂-CH(NHR³''')-C(=O)-OH]

wherein R³'' and R³''' are amino protecting groups to form the protected triamine of formula XIV

XIV

[structure of protected triamine]

wherein R³', R³'', R³''' and R¹ are as above;

d1) converting the protected triamine of formula XIV with an acid into the triamine salt of formula II.

Step a1) comprises the transformation of the carboxylic acid of formula X with an alcohol R¹OH in the presence of an activating agent, an amine catalyst and an organic solvent into the respective ester of formula XI.

Since the ester protecting group should be cleavable under basic conditions suitable alcohols R¹OH are those wherein R¹ is $C_{1-7}$ alkyl or phenyl-$C_{1-7}$ alkyl, wherein the phenyl group is optionally substituted with halogen or $C_{1-7}$ alkyl. Particularly suitable are the $C_{1-4}$ aliphatic alcohols such as methanol or ethanol or benzylalcohol. Preferred alcohol is the benzylalcohol.

It is important that the amino protecting groups R³', R³'' and R³''' are different from R⁴ with regard to the conditions for their removal. Suitably an amino protecting group which is cleavable under acidic conditions such as the preferred Boc group is selected for R³', R³'' and R³'''.

For R⁴ amino protecting groups which are cleavable under basic conditions or by way of hydrogenolysis such as FMOC (basic conditions) or Z (hydrogenolysis) are preferably selected. FMOC is the preferred amino protecting group for R⁴.

Suitable activating agents can be selected from the classical carbodiimides known to the skilled in the art such as N,N'-dicyclohexyl carbodiimide (DCC), N,N'-diisopropyl carbodiimide (DIC) or 1-ethyl-3-(3-dimethylaminopropyl) carbodiimide (EDC), but preferably DCC is used.

The presence of an amine catalyst, preferably 4-(dimethylamino) pyridine is advantageous for the esterification.

The esterification is as a rule performed at a temperature from 20° C. to 50° C. in an aprotic organic solvent such as halogenated hydrocarbons like dichloromethane.

Step b1) in a first step involves the removal of the amino protecting group R⁴, preferably Fmoc with an aliphatic amine in the presence of an organic solvent.

Expediently the aliphatic amine is a secondary aliphatic amine such as dimethylamine, diethylamine, morpholine or piperazine. Preferably diethyl amine is applied.

The reaction is as a rule performed in a suitable organic solvent such as in polar aprotic solvents like tetrahydrofuran at reaction temperatures between 20° C. and 50° C.

Excess amine can suitably be removed by aceotropic distillation with a suitable solvent such for instance with acetonitrile.

In a second step of step b1) the free amine is transformed into an amine salt of formula XII with a suitable acid.

Suitable acids are mineral acids like hydrochloric acid or phosphoric acid or sulfonic acids. Preferably sulfonic acids such as methanesulfonic acid or p-toulenesulfonic acid and more preferably methanesulfonic acid can be used.

X accordingly stands for the anion of the acid applied.

Since the free amine is as a rule not isolated the reaction can take place in the acetonitrile used in step b1) usually at room temperature.

The formed amine salt of formula XII can as a rule be isolated by filtration.

The amine salt of formula XII

XII

[structure: X⁻, R³'-HN-CH₂CH₂CH₂-CH(N⁺H₃)-C(=O)-O-R¹]

wherein $R^1$ and $R^{3'}$ are amine protecting groups and $X^-$ is an anion of an acid are compounds not known in the art and therefore constitute are a further embodiment of the present invention.

In a further preferred embodiment in the amine salt of formula XII $R^1$ is benzyl, $R^{3'}$ is Boc and X is the anion of methanesulfonic acid.

Step c1) involves the coupling of the amine salt of formula XII wherein $R^1$, $R^{3'}$ and X are as above, but preferably wherein $R^1$ is benzyl, $R^{3'}$ is Boc and X is the anion of methanesulfonic acid with the hexanoic acid derivative of formula XIII wherein $R^{3''}$ and $R^{3'''}$ are as above, but preferably are Boc with a coupling agent in the presence of an amine base and an organic solvent and the formation of the protected triamine of formula XIV.

The coupling can follow the classical methods known to the skilled in the art using a carbodiimide coupling agent like DCC (N,N'-Dicyclohexyl carbodiimide), EDC (N-(3-dimethylaminopropyl)-N'-ethylcarbodiimide) or EDC.HCl (N-(3-dimethylaminopropyl)-N'-ethylcarbodiimide hydrochloride and an additive like HOBt (1-hydroxybenztriazole), HOSu (N-hydroxysuccinimide), TBTU (N,N,N',N'-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combinations thereof such as TBTU/HOBt or HBTU/HOAt.

In a preferred embodiment n-propylphosphonic acid anhydride (T3P) is selected as coupling agent together with a tertiary amine base, like triethylamine or N-ethyldiisopropylamine but preferably with N-ethyldiisopropylamine.

The hexanoic acid derivatives of formula XIII, particularly the Boc protected derivative are compounds which are commercially available.

The coupling reaction usually takes place in a polar aprotic solvent like acetonitrile or tetrahydrofuran or mixtures thereof at reaction temperatures in the range of 0° C. and 50° C.

The isolation of the crude protected triamine of formula XIV can happen by removing the solvents. Subsequent crystallization for instance with acetonitrile leads to a product with high purity which can readily be used for the next step d1).

In a preferred embodiment in the protected triamine of formula XIV $R^1$ is benzyl and $R^{3'}$, $R^{3''}$ and $R^{3'''}$ are Boc.

Step d1) involves the conversion of the protected triamine of formula XIV wherein $R^1$, $R^{3'}$, $R^{3''}$ and $R^{3'''}$ are as above, preferably wherein $R^1$ is benzyl and $R^{3'}$, $R^{3''}$ and $R^{3'''}$ are Boc with an acid in the presence of an organic solvent into the triamine salt of formula II.

Suitable acids are mineral acids like hydrochloric acid or phosphoric acid, trifluoroacetic acid or sulfonic acids. Preferably sulfonic acids such as methanesulfonic acid or p-toulenesulfonic acid and more preferably methanesulfonic acid can be used.

Preferably an excess of 4 eq to 10 eq of the respective acid is used.

The reaction is usually performed in a suitable polar aprotic solvent at a reaction temperature from 20° C. to 80° C.

In a preferred embodiment of the present invention the conversion is performed in a polar aprotic solvent which prevents the resulting triamine salt of formula II to crystallize. Particularly preferred solvent is acetonitrile which leaves the resulting triamine salt of formula II in the form of an emulsion which can readily be used for the subsequent coupling with the tetrahydropyran acid of formula II in step a).

Synthesis of the Tetrahydropyran Acid of Formula III (Building Block B):

The process for producing the tetrahydropyran acid of formula III comprises a2) the transformation of a diol of formula XX

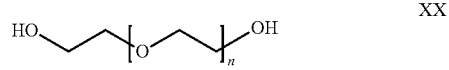

wherein n is an integer between 0 and 10 into the alcohol ester of formula XXI

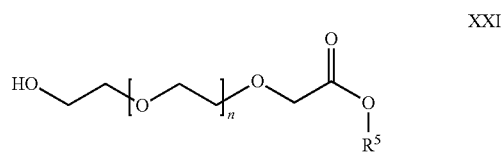

wherein n is as above and $R^5$ is an ester protecting group;

b2) the coupling of the alcohol ester of formula XXI with a tetrahydropyran derivative of formula XXII

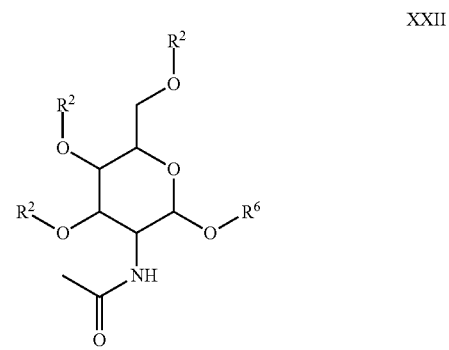

wherein $R^2$ and $R^6$ independent of each other are hydroxy protecting groups to form a tetrahydropyran ester of formula XXIII

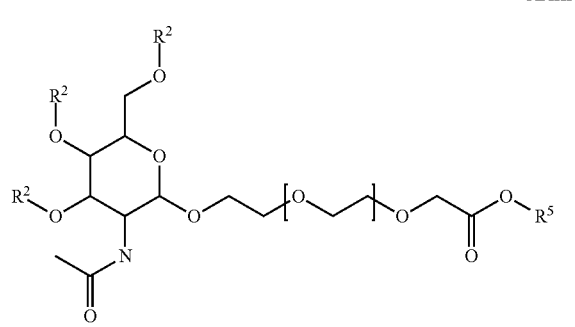

wherein $R^2$ and $R^5$ are as above;

c2) the removal of the ester group $R^5$ to form the tetrahydropyran acid of formula III.

Step a2) requires the transformation of the diol of formula XX into the alcohol ester of formula XXI.

The diol of formula XX is characterized by n repeating —($CH_2$—)—O— units. The integer n is as a rule selected between 0 and 10, but preferably between 0 and 5, more preferably between 0 and 2. Preferred diol is the commercially available 2-[2-(2-hydroxyethoxy) ethoxy]ethanol (n=1).

In a first step of step a2) the diol of formula XX is deprotonated with an alkali metal alcoholate.

Suitable alkali metal alcoholates are sodium- or potassium-tertiary alcoholates such as sodium- or potassium t-butylate or sodium- or potassium amylate.

For the deprotonation a polar protic or polar aprotic solvent such as N,N-dimethylformamide or tertiary alcohols like t-butanol or 2-methyl-2-butanol may be present and the reaction can take place at 50° C. to 120° C.

In a second step of step a2) the acetic acid moiety is introduced with a halogen acetic acid or with a suitable salt thereof.

Suitable halogen acetic acid is bromo- or chloro-acetic acid or the alkali metal salts thereof. In a preferred embodiment a salt of the halogen acetic acid is employed, more preferably sodium chloroacetate is used.

The reaction can take place in a polar protic or polar aprotic solvent, usually in the same solvent as in the previous step.

The reaction temperature depends on the solvent but as a rule is selected between 50° C. and 120° C.

In the third step of step a2) the intermediary ester salt is without its isolation transformed into the alcohol ester of formula XXI.

The formation of the alcohol ester means the introduction of the ester protection group $R^5$.

While the art knows many possibilities to protect an ester the benzyl group was found to be most suitable. Its introduction can happen with a benzyl halogenide or a benzyl sulfonyl ester but preferably with benzyl bromide.

The esterification can take place in a polar aprotic solvent, usually in the same solvent as in the previous step at a reaction temperature of 20° C. to 120° C.

The isolation of the alcohol ester from the reaction mixture can happen by way of extraction with a suitable solvent such as with methyl t-butyl ether and removing of the solvent. Step b2) requires the reaction of the alcohol ester of formula XXI with the tetrahydropyran derivative of formula XXII in the presence of an acid and an organic solvent to form the tetrahydropyran ester of formula XXIII While the art knows many hydroxy protecting groups $R^2$ and $R^6$ are preferably acetyl.

The tetrahydropyran derivative of formula XXII, particularly the acetyl derivatives are compounds which are commercially available.

Suitable acids are halogenated sulfonic acids such as the preferred trifluoromethanesulfonic acid.

The reaction is usually performed in the presence of polar aprotic solvent like dichloromethane at reaction temperatures of 0° C. to 40° C.

In a preferred embodiment the generated acetic acid is continuously distilled off in the course of the reaction.

After neutralization of the reaction mixture the tetrahydropyran ester of formula XXIII can be isolated by removing the solvents. The crude product can be purified by silica chromatography with N-heptane/acetone or preferably tert-.butyl methyl ether/acetone as mobile phase.

In a preferred embodiment in the tetrahydropyran ester of formula XXIII $R^2$ is acetyl and $R^6$ is benzyl.

Step c2) refers to the removal of the ester group $R^6$.

The removal of an ester groups is in principle known to the skilled in the art and well described in literature.

As a preferred embodiment step c2) involves a catalytic hydrogenation with hydrogen in the presence of a hydrogenation catalyst to remove the benzyl group and the formation of the tetrahydropyran acid of formula III.

Typical hydrogenation catalyst for the removal of the benzyl group is palladium on carbon (Pd/C).

The reaction is usually performed in the presence of polar aprotic solvent like tetrahydrofuran at reaction temperatures between 10° C. and 30° C. and at a hydrogen pressure of 1 bar to 5 bar.

The tetrahydropyran acid of formula III can, after filtering off the catalyst, directly be used in solution for the subsequent coupling in step a) of the process of the present invention.

In the preferred tetrahydropyran acid of formula III $R^2$ is acetyl.

In an another embodiment the alcohol ester of formula XXI can be prepared with a process comprising the steps a3) the diazotization of an 2-amino acetate of formula XXV

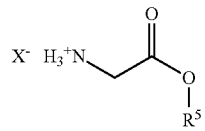

XXV wherein $R^5$ is as above and X is a halogen atom with a nitrite salt to form the 2-diazo compound of formula XXVI

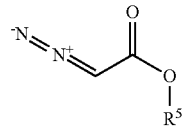

XXVI wherein $R^5$ is as above; and b3) the transformation of the 2-diazo compound of formula XXVI with the diol of formula XX into the desired alcohol ester of formula XXI.

Step a3) requires the diazotization amino of the 2-amino acetate of formula XXV and the formation of the 2-diazo compound of formula XXVI.

The amino acetate of formula XXV is a commercially available compound which is suitably applied as hydrochloride (X=Cl).

The diazotization is as a rule performed with an alkali nitrite, preferably with sodium nitrite in the presence of a solvent mixture of water and a non-polar aprotic solvent at a reaction temperature of −10° C. to 10° C., preferably 0° C. to 5° C.

Suitable non-polar aprotic solvents can be selected from methyl tert. butyl ether, tetrahydrofuran, 2-methyl tetrahydrofuran, cyclopentyl methyl ether, dichloromethane and toluene. Preferably toluene is used in a 1:1 v/v mixture with water.

The 2-diazo compound of formula XXVI obtained is kept dissolved in the organic phase for the subsequent transformation in step b3).

Step b3) requires the transformation of the 2-diazo compound of formula XXVI with the diol of formula XX.

As outlined above the diol of formula XX is characterized by n repeating —(CH$_2$—)—O— units. The integer n is as a rule selected between 0 and 10, but preferably between 0 and 5, more preferably between 0 and 2. Preferred diol is the commercially available 2-[2-(2-hydroxyethoxy) ethoxy] ethanol (n=1).

The reaction can be performed in the presence of a Lewis acid and a non-polar aprotic solvent at −10° C. to 10° C., preferably 0° C. to 5° C.

The non-polar aprotic solvent is as a rule the same as used in step a3).

Typical Lewis acids can be selected from boron trihalogenides, such as boron trifluoride and its commercially available adducts like boron trifluoride diethyl etherate, or rhodium (II) acetate or copper (II) trifluoromethanesulfonate. Preferably boron trifluoride in the form of the diethyl etherate is applied.

The alcohol ester of formula XXI can be isolated from the reaction mixture by common work up procedures involving separating the organic layer, removing the solvent by evaporation and optionally further purifying the crude via chromatography.

The alcohol ester of formula XXI can then readily be used for the subsequent step b2).

Assembly of Building Block A and B

Step a) requires the coupling of the a triamine salt of formula II with the tetrahydropyran acid of formula III in the presence of a peptide coupling agent, an amine base and an organic solvent to form the GalNAc ester of formula IV.

As described above both the triamine salt of formula II and the tetrahydropyran acid of formula III can preferably be used without isolation from the reaction mixture resulting from their synthesis.

As outlined above in the preferred tetrahydropyran acid of formula III $R^2$ is acetyl and in the preferred triamine salt of formula II $R^1$ is benzyl and X is the anion of methanesulfonic acid.

The coupling can follow the classical methods known to the skilled in the art using a carbodiimide coupling agent like DCC and an additive like HOBt (1-hydroxybenztriazole), HOSu (N-hydroxysuccinimide), TBTU (N,N,N',N'-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combination thereof such as TBTU/HOBt or HBTU/HOAt.

In a preferred embodiment n-propylphosphonic acid anhydride (T3P) is selected as coupling agent together with a tertiary amine base like triethylamine or N-ethyldiisopropylamine, but preferably N-ethyldiisopropylamine.

The coupling reaction usually takes place in a polar aprotic solvent like acetonitrile or tetrahydrofuran or mixtures thereof at reaction temperatures in the range of 20° C. and 70° C.

The formed methanesulfonic acid and the excess amine base and coupling agent can after completion of the coupling reaction be removed by precipitating the crude product in a suitable organic solvent such as in 2-propanol.

In an alternative and preferred embodiment steps a) and b) can be combined and performed in one step without isolating the GalNAc ester of formula IV. Accordingly the reaction mixture from step a) can directly be treated with the mineral base as outlined in step b) below.

In the preferred GalNAc ester of formula IV $R^1$ is benzyl and $R^2$ is acetyl.

Step b) requires the removal of the ester protecting group $R^1$ and of the hydroxy protecting groups $R^2$ in the presence of a mineral base to form the GalNAc acid salt of formula V.

As a rule the GalNAc ester of formula IV is dissolved in polar organic solvent, particularly in an alcohol like methanol.

M represents a metal kation, usually an alkali or earth metal kation such as lithium, sodium, potassium, rubidium, calcium or magnesium, but preferably sodium, potassium or calcium, more preferably sodium.

A suitable mineral base accordingly is an alkali or earth alkali metal hydroxide selected from sodium-, potassium- or calcium-hydroxide, typically applied in the form of an aqueous solution. Preferably aqueous sodium hydroxide is used in an excess of 11 eq to 25 eq.

The reaction can be performed at a temperature of 0° C. to 40° C.

The crude product can be isolated by evaporation of the solvent. Further purification of the product can be achieved by preparative reversed phase chromatography using a polar stationary phase and a polar mobile phase.

A preferred polar mobile phase was found to be mixtures of aqueous sodium hydrogen carbonate and acetonitrile which were applied with changing gradients.

Concentration of the selected fractions from the chromatography provides a pure GalNAc acid salt of formula V.

In the preferred GalNAc acid salt of formula V $R^1$ is benzyl, $R^2$ is acetyl and M is sodium.

No concentration is necessary in case the GalNAc salt of formula V is subjected to the optional step c) which comprises the transformation of the GalNAc acid salt of formula V into the GalNAc acid derivative of formula I.

The transformation can be performed by ion exchange with a suitable kation exchanger or alternatively by neutralization with a suitable acid, for instance phosphoric acid or sulfonic acids like methane sulfonic acid.

In case the desired GalNAc acid derivative of formula I is isolated the transformation can preferably take place in a methanolic solution. Removal of the solvent renders the desired product in high purity and yield.

Alternatively, in case the GalNAc acid derivative of formula I is directly subjected to the conjugation with oligonucleotides the transformation is suitably performed in a polar aprotic solvent like N,N'-dimethylformamide.

As a further alternative the GalNAc acid derivative of formula I can be transformed back into a GalNAc salt of formula V in the presence of a suitable mineral base, as outlined above. This alternative would in principle allow changing the metal cation.

The term "salt" in the context of the GalNAc acid derivative of formula I accordingly means an alkali or earth metal salt with a kation selected from lithium, sodium, potassium, rubidium, calcium or magnesium, but preferably sodium, potassium or calcium, more preferably sodium.

Conjugation to Oligonucleotides

The GalNAc acid derivative of formula I or the GalNAc acid salt of formula V can be used as initially described for the preparation of therapeutically valuable GalNAc oligonucleotide conjugates.

The term oligonucleotide as used herein is defined as it is generally understood by the skilled person as a molecule comprising two or more covalently linked nucleosides. For use as an therapeutically valuable oligonucleotide, oligonucleotides are typically synthesized as 7-30 nucleotides in length.

The oligonucleotides may consist of DNA, RNA, modified RNA or LNA nucleoside monomers or combinations thereof. The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

The oligonucleotides may also contain amino linkers at the 5' end of the oligonucleotide such as for instance a C-6-amino linker.

The preparation of GalNAc polynucleotide conjugates comprise the steps a3) preparing the GalNAc acid derivative of formula I or the GalNAc acid salt of formula V according to the present invention as described above and b3) conjugating the GalNAc acid derivative of formula I or the GalNAc acid salt of formula V under peptide coupling conditions with a polynucleotide.

The conjugation with the GalNAc acid salt of formula V is preferred.

The peptide coupling conditions are classical methods known to the skilled in the art using a carbodiimide coupling agent like DCC (N,N'-Dicyclohexylcarbodiimide), EDC (N-(3-dimethylaminopropyl)-N'-ethylcarbodiimide) or EDC.HCl (N-(3-dimethylaminopropyl)-N'-ethylcarbodiimide hydrochloride and an additive like HOBt (1-hydroxybenztriazole), HOSu (N-hydroxysuccinimide), TBTU (N,N,N',N'-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combinations thereof such as TBTU/HOBt or HBTU/HOAt.

By way of example the US Patent Application Publication 2011/0207799 can be cited for reference of a conjugation of GalNAc derivatives to oligonucleotides.

EXAMPLES

Abbreviations
AcOH acetic acid
DMAP 4-(dimethylamino)-pyridine
DMF N, N'-dimethylformamide
EtOH ethanol
MeOH methanol
rt room temperature
THF tetrahydrofuran
TBME tert.-butyl methyl ether Building Block A Example 1

Benzyl (2S)-6-(tert-butoxycarbonylamino)-2-(9H-fluoren-9-ylmethoxycarbonylamino)hexanoate 234.0 g (500.0 mmol) (2S)-6-(tert-butoxycarbonylamino)-2-(9H-fluoren-9-ylmethoxycarbonylamino) hexanoic acid was suspended in 500 ml dichloromethane, 62.0 ml (600 mmol, 1.2 eq) benzyl alcohol and 3.05 g DMAP (25.0 mmol, 0.05 eq) were added. The solution was cooled to 0-5° C. in the course of 40 min, a solution of 108.0 g (525.0 mmol, 1.05 eq) N,N'-dicyclohexyl carbodiimide in 500 ml dichloromethane, was added dropwise. The white suspension was stirred for 1 h at 0-5° C. and then for 15 h at room temperature. The suspension was filtered over a G3 glass filter, the white filter cake was washed portion-wise with total 250 ml dichloromethane. The filtrate was evaporated at 650-10 mbar/1 h to obtain a yellow oil, which was in dissolved in 2.0 L ethyl acetate, extracted with 2.0 L 0.5M hydrochloric acid, 2.0 L 1M NaHCO₃ and 1.0 L brine, the organic layer was evaporated to dryness at 40° C./150-10 mbar/5 h to obtain 291.1 g crude benzyl (2S)-6-(tert-butoxycarbonylamino)-2-(9H-fluoren-9-ylmethoxycarbonylamino) hexanoate as white solid in 104% yield and 96.4% purity (HPLC area-%; contains ca. 5% benzyl alcohol). The material was used in the next step without further purification. MS: m/z=459.22735 (M-boc+H)⁺.

Example 2

Benzyl (2S)-2-amino-6-(tert-butoxycarbonylamino)hexanoate methanesulfonic acid salt

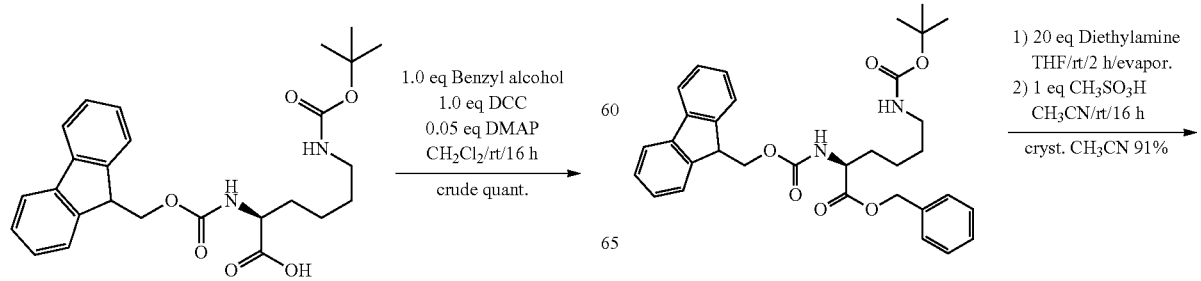

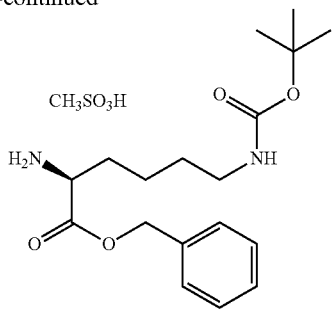

291.1 g Benzyl (500.0 mmol) (2S)-6-(tert-butoxycarbonylamino)-2-(9H-fluoren-9-ylmethoxycarbonylamino)hexanoate (HPLC purity; 95.8%; contains ca. 5% benzyl alcohol) were dissolved in 1.4 L THF at room temperature. Within 10 min, 1.04 L diethylamine (10.0 mol, 20 eq) were added, the light yellow solution was stirred for 2 h at room temperature and then evaporated at 40° C./200-10 mbar, 200 ml acetonitrile was added and evaporated again to efficiently remove diethylamine at 40° C./100-10 mbar/1 h. Finally, 268.1 g of a yellow oil was obtained, which was dissolved in 2.5 L acetonitrile, stirred for 10 min at room temperature. Insoluble particles were filtered over a glass fiber filter and washed with 500 ml acetonitrile. The filtrate was treated dropwise in the course of 10 min with 34.0 ml methanesulfonic acid at 20° C.-25° C. The formed white suspension was stirred for 17 h at room temperature and filtered over a G3 glass filter. The filter cake was washed portion-wise with 500 ml acetonitrile. The white crystals were dried at 40° C./15 mbar/4 h to obtain 195.8 g benzyl (2S)-2-amino-6-(tert-butoxycarbonylamino)hexanoate methanesulfonic acid salt as white crystals in 91% yield (2 steps) and 99.3% purity (HPLC area-%). MS: m/z=337.2149 (M+H)+.

Example 3

Benzyl (2S)-2-[[(2S)-2,6-bis(tert-butoxycarbonylamino)hexanoyl]amino]-6-(tert-butoxycarbonylamino)hexanoate

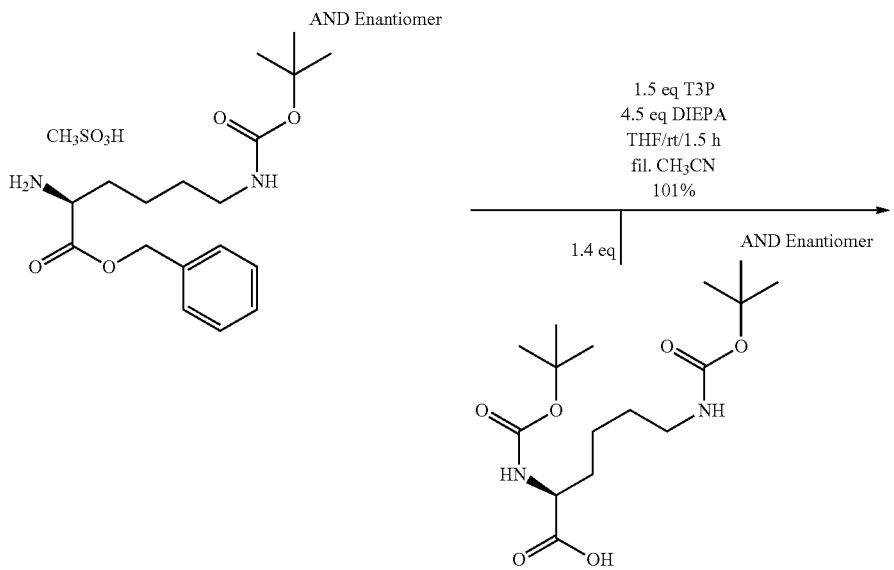

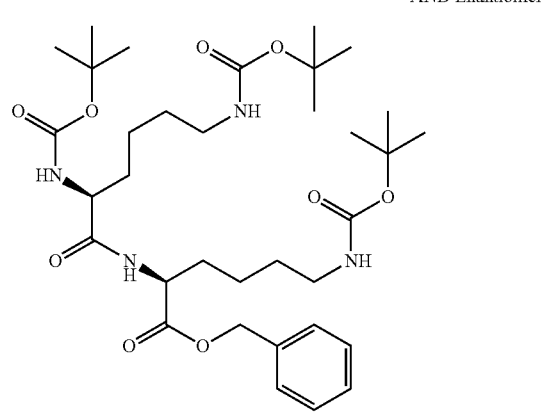

190.0 g (439.0 mmol) Benzyl (2S)-2-amino-6-(tert-butoxycarbonylamino)hexanoate methanesulfonic acid salt were suspended in 1.9 L THF at room temperature. 335 ml (1.98 mol, 4.5 eq)N-ethyldiisopropylamine were added whereby the temperature slightly decreased to 15° C. Next, 213 g (615 mmol, 1.4 eq) (S)-2,6-bis((tert-butoxycarbonyl) amino)hexanoic acid were added and the white suspension was stirred at room temperature for 20 min. 390 ml n-propylphosphonic acid anhydride (T3P as cyclic trimer 50% in ethyl acetate, 659 mmol, 1.5 eq) were added dropwise in the course of 20 min at 20-25° C. (cooled in a cool water bath). The resulting light yellow, cloudy solution was stirred at room temperature for 1.5 h, transferred to a separating funnel, diluted with 1.9 L TBME and extracted with 1.9 L water, 1.9 L 0.5M hydrochloric acid, 1.9 L0.5M NaOH, 1.9 L water and 1.9 L brine. The separated, still cloudy organic layer was filtered over a glass fiber filter, the filter was washed with 100 ml TBME and the combined filtrates were evaporated at 40° C./100 mbar/1 h, 1.0 L TBME (to aceotropic remove water) were added again and evaporated at 40° C./250-10 mbar/1 h to obtain crude 296.4 g as white solid residue.

The crude solid was treated with 500 ml acetonitrile and the cloudy solution was heated to 60-65° C. for 10 min. The mixture was cooled to 20-25° C., stirred for 10 min, filtered over a glass fiber filter and washed with 50 ml acetonitrile. The light yellow solution was evaporated at 40° C./100-10 mbar/4 h to obtain 295 g benzyl (2S)-2-[[(2S)-2,6-bis(tert-butoxycarbonylamino)hexanoyl]amino]-6-(tert-butoxycarbonylamino)hexanoate as off-white solid in a yield of 101% (HPLC purity: 100%, diastereomer purity (SS) 98.6%) which was used without further purification in the next step. MS: m/z=565.3741 (M-boc+H)$^+$.

Example 4

Benzyl (2S)-6-amino-2-[[(2S)-2,6-diaminohexanoyl] amino]hexanoate tri-methanesulfonic acid salt

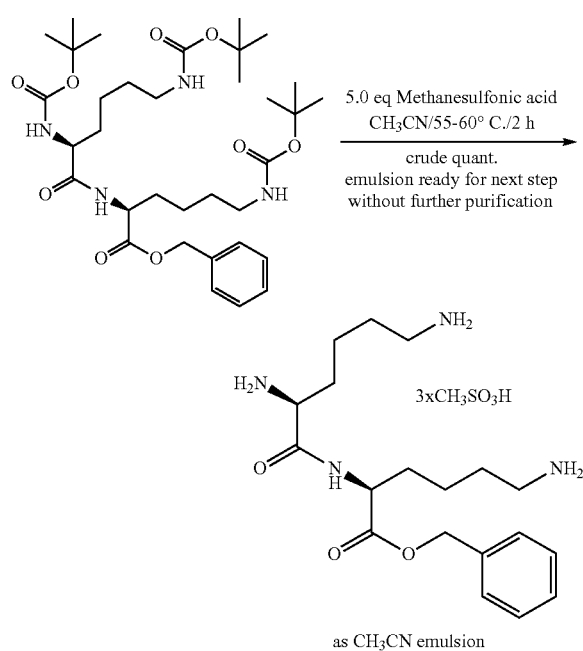

124.0 g (187 mmol) benzyl (2S)-2-[[(2S)-2,6-bis(tert-butoxycarbonylamino)hexanoyl]amino]-6-(tert-butoxycarbonylamino)hexanoate was suspended in 1.25 L acetonitrile. 61.0 ml (935.0 mmol, 5.0 eq) methanesulfonic acid was added at 20-25° C. in the course of 10 min (gas evolution). The resulting orange suspension was heated in 40 min to 55-60° C. and stirred for another 1 h at 55-60° C. The orange-red emulsion was cooled to room temperature (debocation was controlled by $^1$H-NMR) and used without further purification in the A+B assembly step, example 8. MS: m/z=365.2558 (M+H)$^+$.

Building Block B

Example 5a

Benzyl 2-[2-[2-(2-hydroxyethoxy)ethoxy]ethoxy] acetate

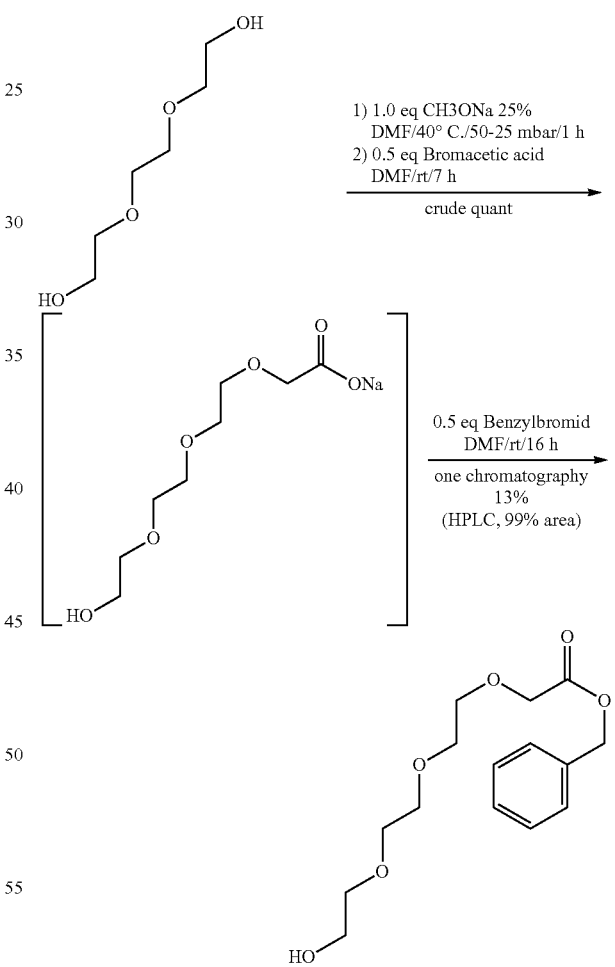

30.0 g (200.0 mmol), 2-[2-(2-Hydroxyethoxy)ethoxy] ethanol were dissolved in 50 ml DMF, at 20-25° C., then, 46.0 ml sodium methoxide 25% (200.0 mmol, 1.0 eq) in methanol were added. The formed solution was evaporated at 40° C./50 mbar/0.5 h (remove of 40 ml solvent), 50 ml DMF was added again and evaporated at 40° C./20 mbar/0.5 h (remove of 15 ml solvent), To the slightly jellylike suspension a solution of 13.9 g bromoacetic acid (100 mmol, 0.5 eq) in 50 ml DMF was added at 20-25° C. and the mixture was stirred for 6 h. 11.9 ml benzyl bromide (100 mmol, 0.5 eq) was added and the mixture stirred for another 16 h at 20-25° C. The reaction mixture was then treated with 200 ml brine and extracted with 200 ml TBME. The separated TBME layer was extracted with 200 ml brine, the separated TBME layer was then dried with anhydrous sodium sulfate, filtered and evaporated at 40° C./300-10 mbar/1 h to obtain crude 23.9 g benzyl 2-[2-[2-(2-hydroxyethoxy)ethoxy]ethoxy]acetate.

After chromatography (600 g silica 60 (0.063-0.2 mm), mobile phase: ethyl acetate) a total of 7.85 g benzyl 2-[2-[2-(2-hydroxyethoxy)ethoxy]ethoxy]acetate as colorless oil was isolated in 13% yield and 99.0% purity (HPLC area-%). MS: m/z=299.1517 (M+H)$^+$.

Example 5b

Benzyl 2-[2-[2-(2-hydroxyethoxy)ethoxy]ethoxy] acetate

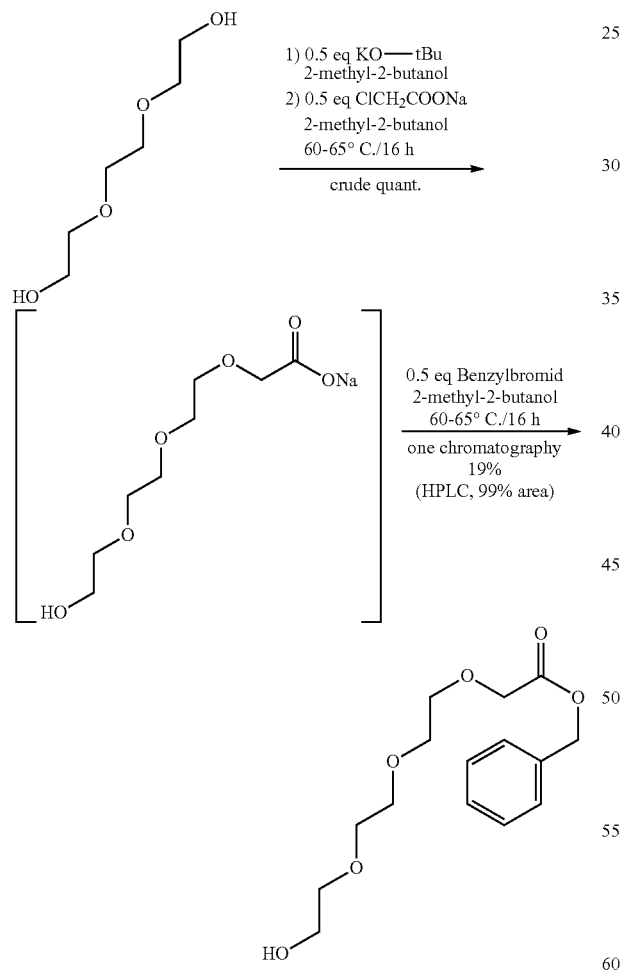

11.2 g potassium tert.-butylate (100.0 mmol, 0.5 eq) was suspended in 70 ml 2-methyl-2-butanol (light exothermic 35° C.), then 30.0 g (200.0 mmol) 2-[2-(2-Hydroxyethoxy) ethoxy]ethanol were added dropwise in the course of 5 min. the dropping funnel were rinsed with 10 ml 2-methyl-2-butanol (temp. increase to 45° C.), the solution was heated to 60-65° C., 11.6 g (100 mmol, 0.5 eq) sodium chloroacetate were added and stirred for 16 h at 60-65° C., then 11.9 ml benzyl bromide (100 mmol, 0.5 eq) were added and the mixture stirred for another 16 h at 60-65° C. The reaction mixture was cooled to rt, then treated with 50 ml water and extracted with 80 ml TBME and 40 ml TBME. The combined TBME layer was washed with 50 ml half saturated brine, the organic layer were evaporated at 40° C./300-10 mbar/1 h to obtain crude 27.0 g benzyl 2-[2-[2-(2-hydroxyethoxy)ethoxy]ethoxy]acetate.

After chromatography (270 g silica 60 (0.063-0.2 mm), mobile phase: start with ethyl acetate/n-heptane 1/1, when pure product are visible, mobile phase were changed to 100% ethyl acetate, total 11.4 g benzyl 2-[2-[2-(2-hydroxyethoxy)ethoxy]ethoxy]acetate as nearby colorless oil was isolated in 19% yield (38% from sodium chloroacetate) and 99.0% purity (HPLC area-%)

Example 5c

Benzyl 2-[2-[2-(2-hydroxyethoxy)ethoxy]ethoxy] acetate

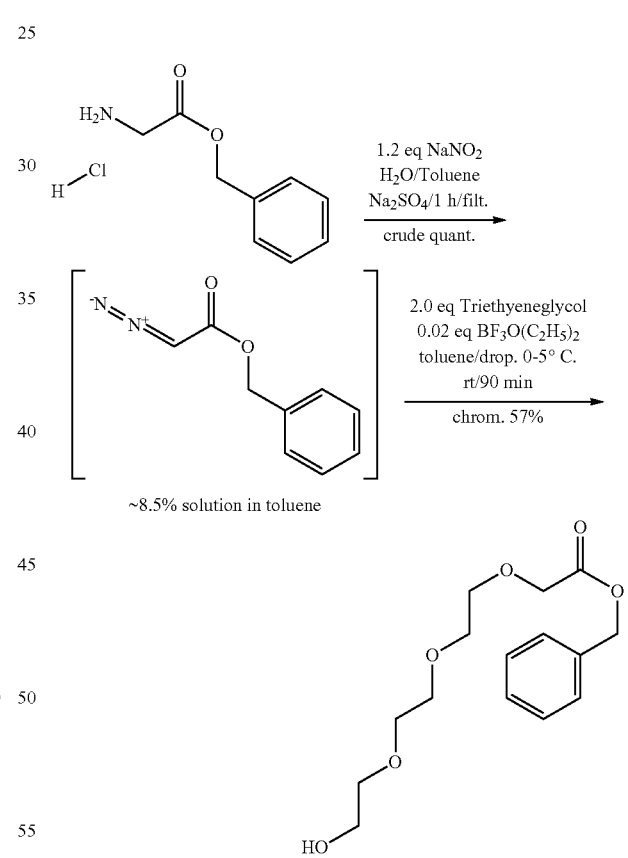

40.3 g (200.0 mmol) Benzyl 2-aminoacetate hydrochloride was dissolved in 340 ml water and 340 ml toluene cooled to 0-5° C., in the course of 60 min a solution of 16.5 g (240 mmol, 1.2 eq) sodium nitrite in 50 ml water was added dropwise at 0-5° C. under vigorous stirring. The reaction mixture was stirred for 3 hour at 0-5° C. The yellow toluene-layer was separated and washed with 340 ml 1M NaHCO$_3$ and 340 ml brine, the separated toluene layer was treated with 60 g sodium sulfate and stirred for 1 hour at 20-25° C. The yellow suspension was filtered and washed with 50 ml toluene. The clear yellow toluene solution contain in maximum 200.0 mmol benzyl 2-diazoacetate (~8.5% in toluene). This solution was added dropwise in the course of 60 min to a cooled 0-5° C. and well stirred mixture of 60.0 g (400 mmol) triethylen glycol and 465 µl (3.67 mmol, 0.02 eq) boron trifluoride diethyl etherate in 170 ml toluene under evolving of nitrogen gas. The yellow reaction mixture was stirred for 90 min at 20-25° C. at which a colorless solution was formed. The solution was extracted with 250 ml brine, the separated organic layer was dried with 60 g sodium sulfate, filtered, washed with 100 ml toluene and evaporated at 40° C./40-10 mbar/1 h to obtain crude 49.9 g benzyl 2-[2-[2-(2-hydroxyethoxy)ethoxy]ethoxy]acetate. Chromatography was performed with a Teledyne Isco CombiFlash (330 g silica 60 (0.035-0.070 mm Teledyne Isco Cat. No. 69-2203-330), mobile phase: gradient with 15% acetone 85% n-heptane in 45 min to 30% and 70%, fraction size 20 ml. The combined fraction gave 33.88 g benzyl 2-[2-[2-(2-hydroxyethoxy)ethoxy]ethoxy]acetate as colorless oil and with an overall yield of 57% and 99.0% purity (HPLC area-%).

Example 6

Benzyl 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetate

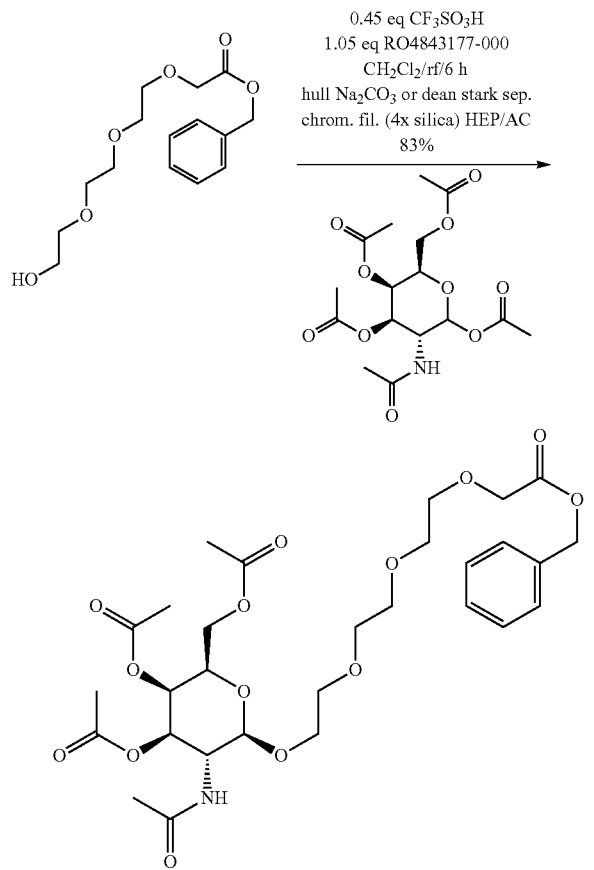

268.0 g Benzyl 2-(2-(2-(2-hydroxyethoxy)ethoxy)ethoxy)acetate (900 mol) were dissolved in 2.4 L dichloromethane. 385.0 g (2S,3R,4R,5R,6R)-3-acetamido-6-(acetoxymethyl)tetrahydro-2H-pyran-2,4,5-triyltriacetate (990 mmol, 1.1 eq) and 12.0 ml trifluoromethanesulfonic acid (135 mmol, 0.15 eq) were added. The suspension was heated to reflux with a dean-stark separator (50 ml, to remove AcOH). After 1 h, 4.50 ml trifluoromethanesulfonic acid (50.7 mmol, 0.05 eq) and 50 ml dichloromethane were added to the orange suspension, the solvent (50 ml) from the dean-stark separator was discharged. Every half hour this procedure was repeated, total 6 times (3 h). After a total of 4.5 h, the red solution was cooled to 10-15° C. and added within 30 min at 20-25° C. to a solution of 1.8 L 1M sodium hydrogen carbonate (1.8 mol, 2.0 eq) ($CO_2$ evolution, pH 7-8). The yellow organic layer was separated and evaporated at 40° C./600-10 mbar/3 h to obtain 585.4 g of crude benzyl 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetate as yellow oil (HPLC purity: 87%). The crude product was dissolved in 700 ml acetone and charged to a preloaded silica column (3.0 kg silica 60; 0.063-0.2 mm). The chromatography was conducted using n-heptane/acetone as mobile phase (gradient from 5:1 to 1:2). The combined collected fractions were evaporated at 40° C./600-10 mbar and dried at 20-25° C./0.3 mbar/3 h to obtain 465.0 g benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate as yellow oil in 83% yield and 100% purity (HPLC area-%). MS: m/z=628.2627 (M+H)⁺.

Example 7

2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid

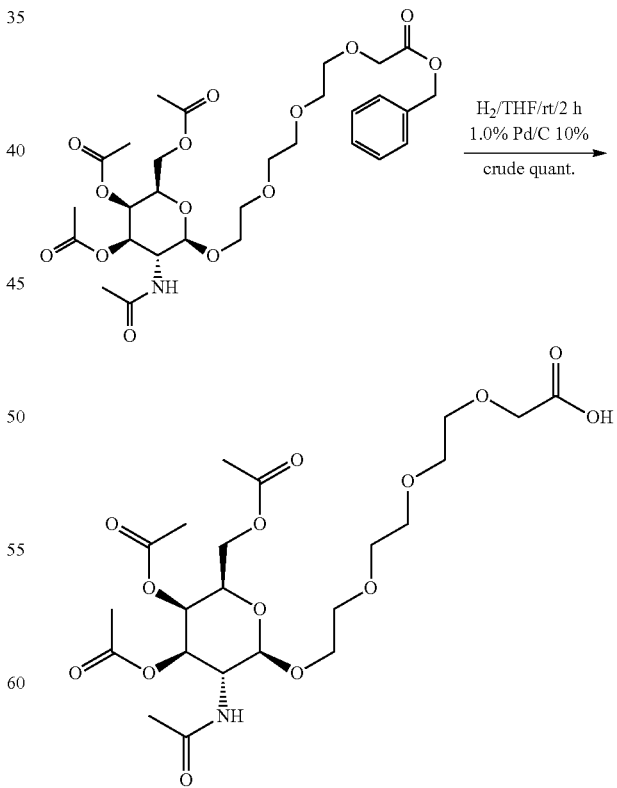

solution in THF

Under argon atmosphere, 456.0 g Benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate (727 mmol) were dissolved in 1.4 L THF. 4.56 g Pd/C 10% were added and the argon atmosphere was replaced with hydrogen (1 bar). The black suspension was hydrogenated at 20-25° C. for 2 h. The hydrogen atmosphere was replaced with argon, the black suspension was filtered and the filter cake was washed portion-wise with total of 400 ml THF. The colorless filtrate (HPLC purity: 71% and 27% toluene) was used without any purification in the A+B assembly step, example 8. MS: m/z=538.2191 (M+H)$^+$.

Assembly of Building Block A and B

Example 8a

Benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate

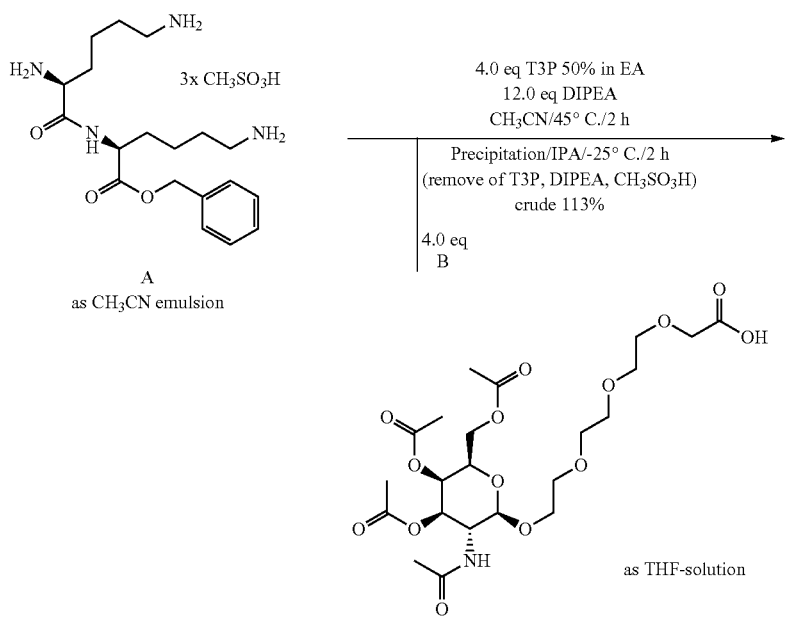

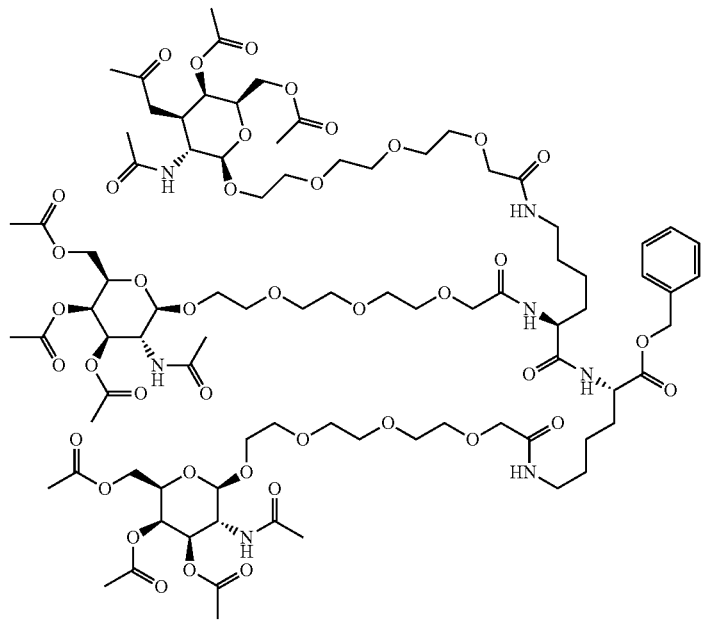

The red-orange solution (~1.4 L) of benzyl (2S)-6-amino-2-[[(2S)-2,6-diaminohexanoyl]amino]hexanoate tri-methanesulfonate (180.0 mmol) from Example 4 was diluted with 3.60 L acetonitrile. At 20-25° C., 365.0 ml N-ethyldiisopropylamine (2.16 mol, 12.0 eq) were added within 5 min. To the formed sticky slurry, a solution (~2.25 L) of 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid (720 mmol, 4.0 eq) from Example 7 was added at 20-25° C. in within 10 min, whereby the temperature slightly increased to 40° C. At 45-50° C., a solution of 425 ml n-propylphosphonic acid anhydride (T3P, trimer 50% in ethyl acetate, 720 mmol, 4.0 eq) was added within 10 min. The reaction solution was stirred for 1 h at 45-50° C. The light yellow solution was cooled to 20-25° C. and evaporated at 40° C./10 mbar/6 h to obtain crude 1.06 kg benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 24.1%). The crude product was precipitated in three portions to remove methansulfonic acid N-ethyldiisopropylamine and residual T3P. 353 g crude product was dissolved in 7.0 L 2-propanol, cooled in 1 h to −25° C., stirred for 1 h at −25° C., filtered over a precooled (−25° C.) G3-glass-filter (no rinse), a part from the precipitated product deposited on the glass-wall from the reactor. All precipitates were dissolved portion-wise from the filter and glass-wall with a total of 1.0 L THF. The combined solutions were evaporated at 40° C./20 mbar/6 h to obtain 390.0 g benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 71.9%), which was used without further purification in the next step. MS: m/z=1923.8438 (M+H)$^+$ Example 8b Sodium; (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate

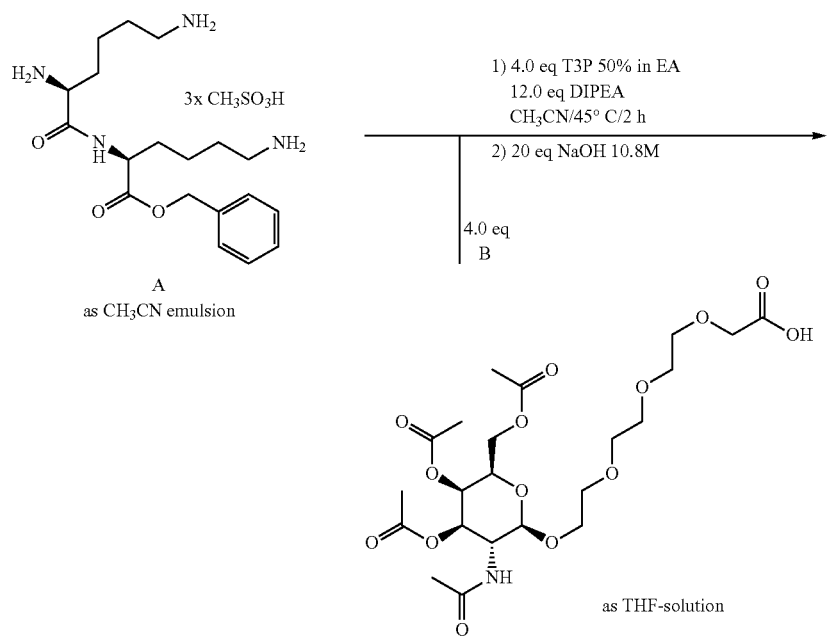

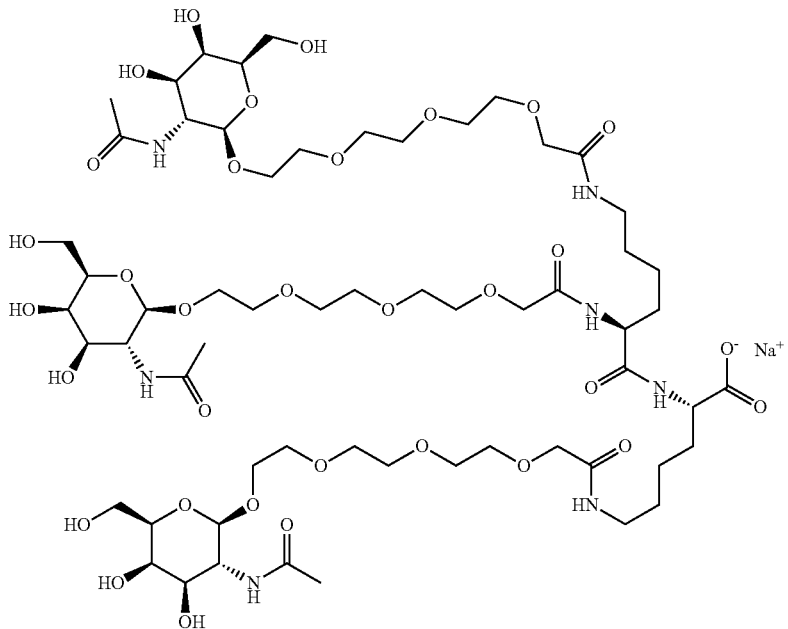

The red-orange solution (~95 ml) of benzyl (2S)-6-amino-2-[[(2S)-2,6-diaminohexanoyl]amino]hexanoate tri-methanesulfonate (12.2 mmol) was diluted with 240 ml acetonitrile. At 20-25° C., 30.0 ml N-ethyldiisopropylamine (2.16 mol, 14.5 eq) were added within 5 min. To the formed sticky slurry, a solution (~150 ml) of 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid (48.8 mmol, 4.0 eq) was added at 20-25° C. in within 10 min, whereby the temperature slightly increased to 40° C. At 45-50° C., a solution of 28.8 ml n-propylphosphonic acid anhydride (T3P, trimer 50% in ethyl acetate, 48.8 mmol, 4.0 eq) was added within 10 min. The reaction solution was stirred for 1 h at 45-50° C. The light yellow solution was cooled to 20-25° C. and evaporated at 40° C./10 mbar/6 h to obtain crude 73.6 g benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetyl] amino]hexanoyl]amino]hexanoate (HPLC purity: 32% area).

68.0 g (11.0 mmol) of the crude product was dissolved in 340 ml methanol 20.0 ml (220 mmol, 20 eq) NaOH 10.8M was added to the light yellow solution, the temperature increased to 32° C., the reaction mixture was stirred for 2.5 h at rt, whereby a suspension was formed (pH 12.0). The suspension was filtered and the filter cake was washed with 100.0 ml methanol, the filtrate was evaporated at 40° C./250-10 mbar/2 h to obtain 41.5 g sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy] ethoxy]acetyl]amino]-2-[[(2S)-2,6-bis[[2-[2-[2-[2-[(2R,3R, 4R,5R,6R)-3-acetamido-4,5-dihydroxy-6-(hydroxymethyl) tetrahydropyran-2-yl]oxyethoxy]ethoxy]ethoxy]acetyl] amino]hexanoyl]amino]hexanoate, which was then purified by preparative reversed phase chromatography, conditions see experiment 9.

Example 9

Sodium; (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate

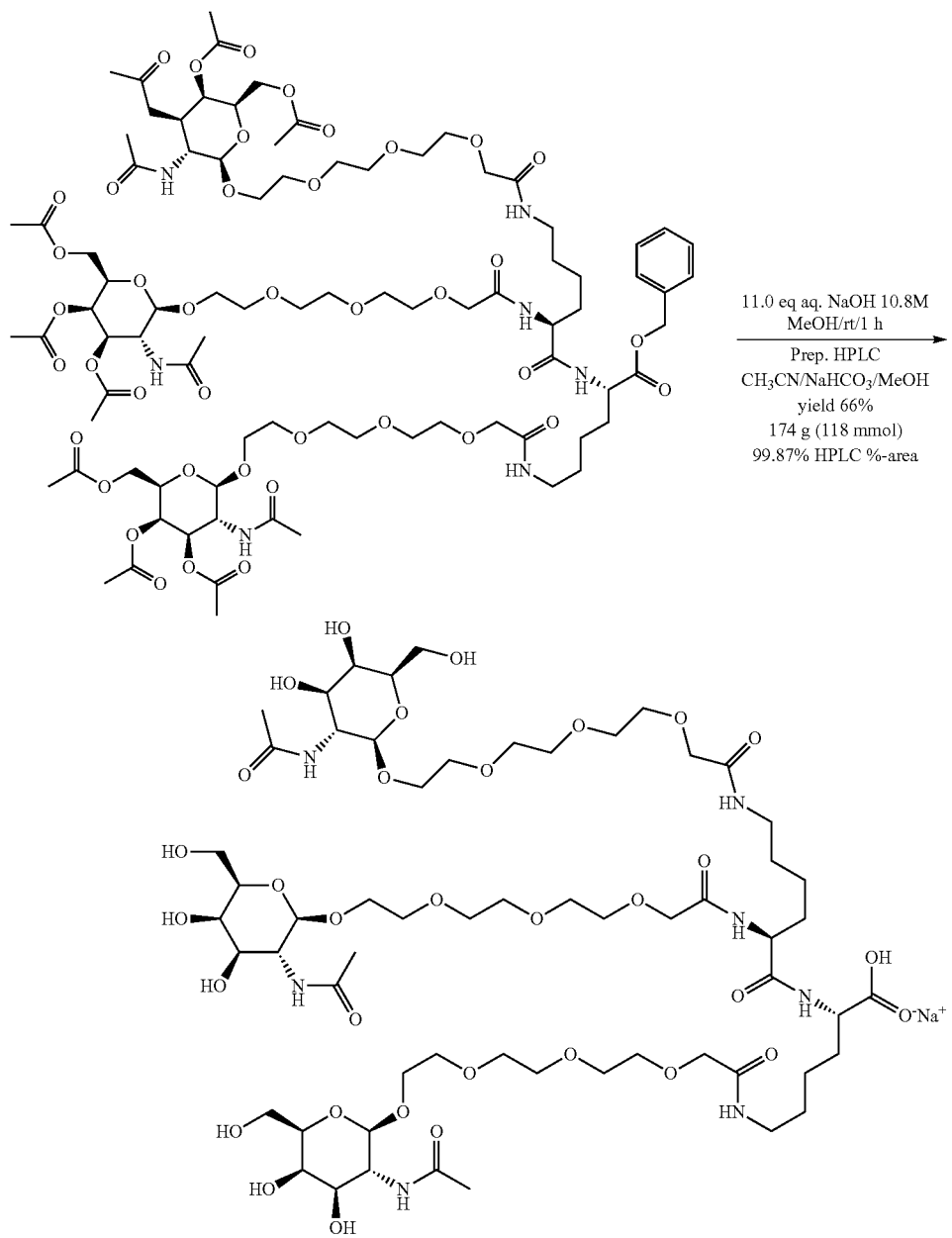

378.0 g (197.0 mmol, crude) Benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate was dissolved in 1.9 L methanol. Within 10 min, 200.0 mL 10.8 M sodium hydroxide solution (2.16 mol, 11.0 eq) were added at 20-25° C. Thereby the temperature increased to 31° C. The light yellow solution was stirred for 2 h at 20-25° C. (pH 13.4), then 80.0 mL 5M ammonium chloride solution were added (pH 10.7). The light yellow solution was then evaporated at 20-25° C./100-20 mbar/5 h and dried at 20-0.5 mbar/1 h to obtain crude 543 g sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate (HPLC purity: 40.1%), which was then purified by preparative reversed phase chromatography.

Column: Triart C18-120 26×15 cm; 10 um;
Mobile phase: A: 2 mM NaHCO₃/B: Acetonitrile;
Gradient:

| Minutes | A | B | Flow(ml/Min) |
|---|---|---|---|
| 0 | 94 | 6 | 700 |
| 2 | 94 | 6 | 700 |
| 20 | 88 | 12 | 700 |
| 20.1 | 10 | 90 | 750 |
| 26 | 10 | 90 | 750 |
| 26.1 | 94 | 6 | 700 |
| 36 | 94 | 6 | 700 |

Thermostatization: room temperature
Detection: 220 nm
Solution: 543 g dissolved in 4500 ml 2 mM NaHCO₃ and filtered (GF5)(=5000 ml (109 mg/ml)
Sample solution/Injection: Per run 200 ml sample=21.8 g (25 runs) Concentration: The combined fractions (46 L) were diluted with 110 L water, this solution were pumped in 3 portions to a RP C18 column and washed with water/MeOH 98/2, then with MeOH eluted and concentrated on a rotary evaporator to obtain 1.18 kg methanolic solution. A quarter of the 1.18 kg methanolic solution of the preparative HPLC purification step, i.e. 295 g were evaporated at 40° C./20 mbar/1 h and then at 20-25° C./0.35 mbar/14 h to dryness to obtain 43.5 g sodium; (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate as amorphous white powder, 99.88% HPLC purity. The remaining three-quarters of the above solution (885 g) were used in the next step. MS: m/z=1452.684 (M−H)⁻.

Example 10

(2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoic acid

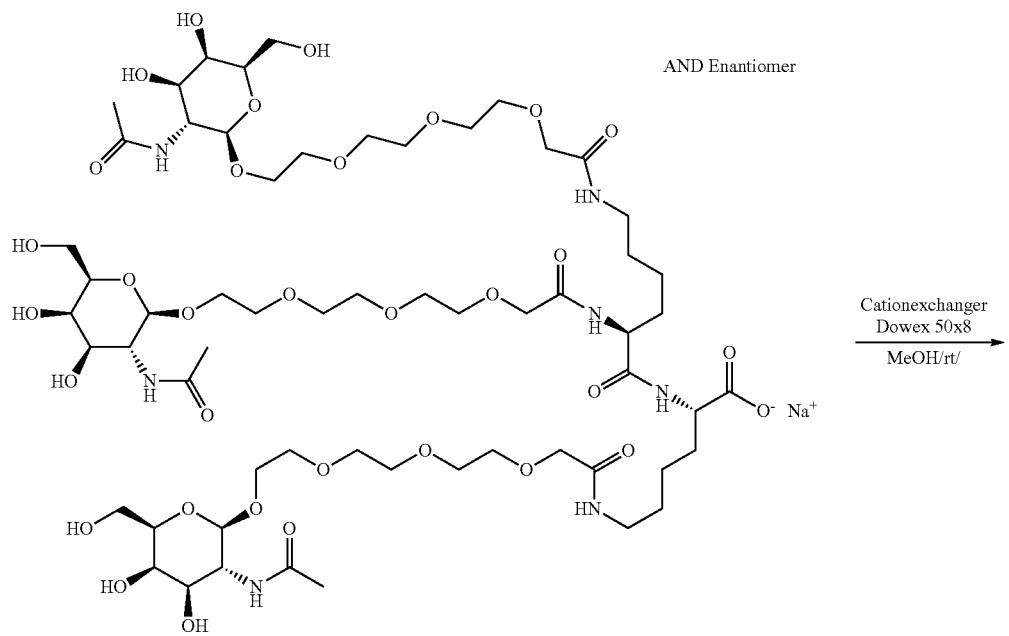

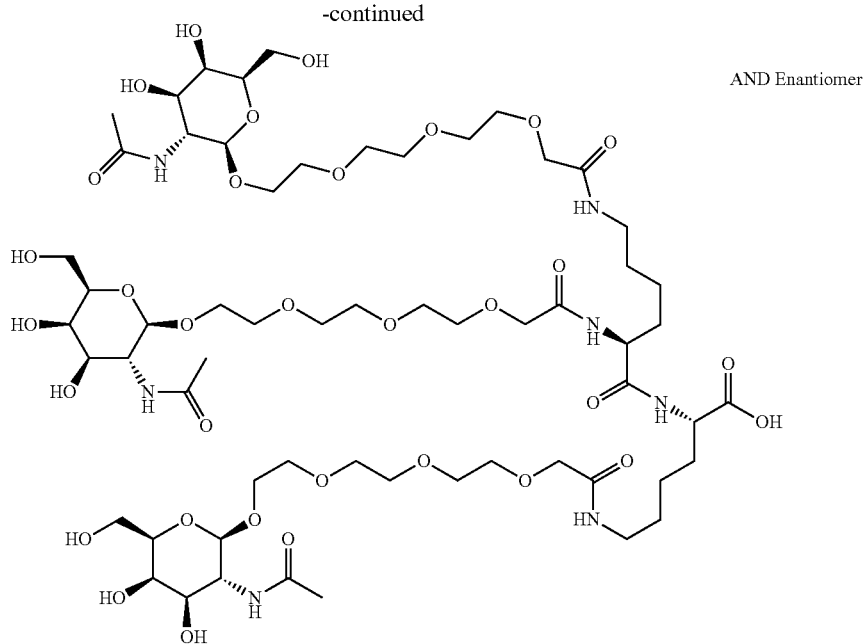

AND Enantiomer

The methanol solution (885 g) from Example 9 was treated at 20-25° C. with 47.9 g Dowex (50×8 kation-exchanger; H₃O⁺ conc. 2.57 mmol/g) stirred for 1 h (pH 3.1), filtered and washed with 200 mL methanol. The filtrate was evaporated at 20-25° C./15-50 mbar and dried at 20-25° C./0.01 mbar/2 h to obtain 128.0 g (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoic acid as a white amorphous powder, 99.77% HPLC purity. MS: m/z=1452.684 (M−H)⁻.

Example 11

Calcium; (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate

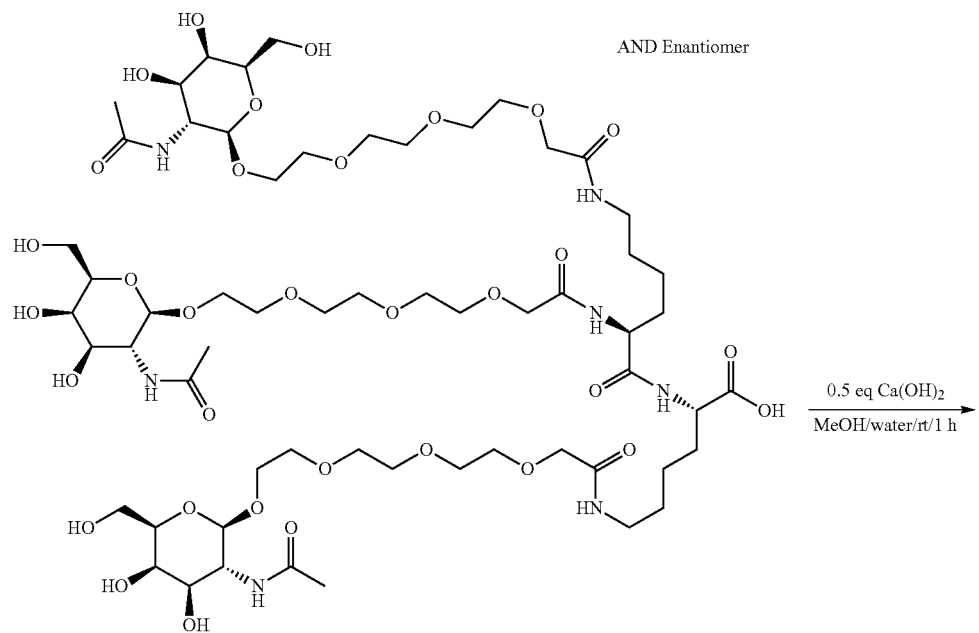

AND Enantiomer 0.5 eq Ca(OH)₂
―――――――――
MeOH/water/rt/1 h

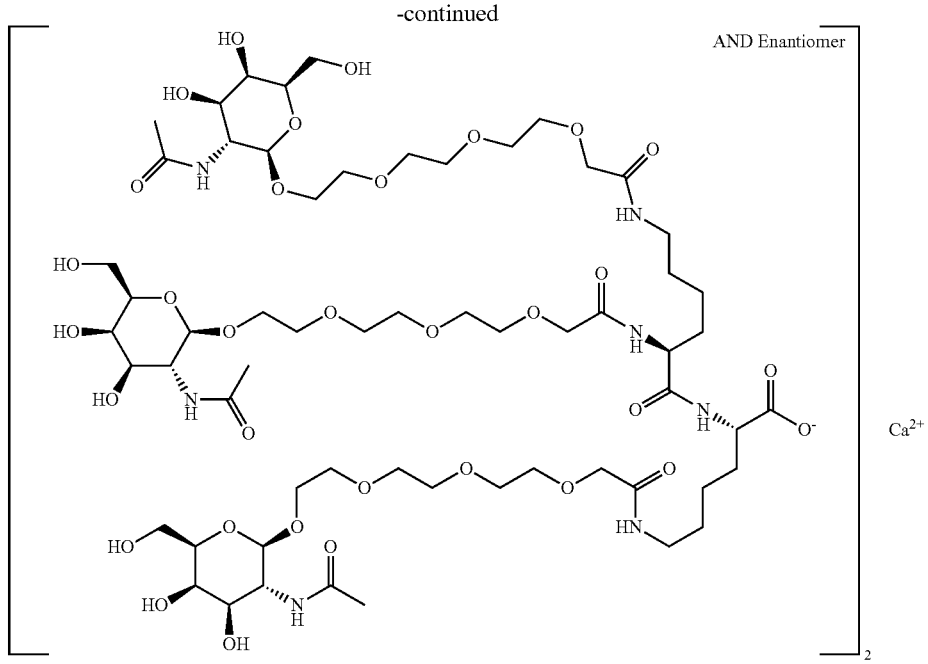

0.10 g (0.068 mmol), (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino] hexanoic acid, was dissolved in 3.0 ml methanol and 0.30 ml water, 2.60 mg (0.034 mmol, 0.5 eq) calcium hydroxide was added and the mixture was stirred for 1 h at room temperature. The light cloudy solution was evaporated at 40° C./200-10 mbar/1 h to obtain 0.11 g as white solid. 99.60% HPLC purity. MS: m/z=1452.684 (M−H)⁻.

Conjugation to Oligonucleotide

Example 11

(in Accordance with Example 15 of US Patent Application Publication 2011/0207799)

(20 mg, 0.014 mmol) (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino] hexanoic acid (GalNAc acid) was co-evaporated with pyridine and dichloromethane. The residue was dissolved in dry DMF (0.9 ml) and a solution of N-Hydroxysuccinimide (HOSu) in DMF (1.6 mg, 0.014 mmol) was added while stirring under an argon atmosphere. At 0° C. a solution of N,N'-Dicyclohexylcarbodiimide (DCC) in DMF (3.2 mg, 0.016 mmol) was slowly added. The reaction was allowed to warm to room temperature and stirred overnight. The formed GalNAc N-hydroxysuccinimid ester was used without further purification for conjugation to RNA.

The RNA used was an amino-modified RNA having the sequence: 5'-(NH$_2$C$_6$)GGAAUCuuAuAuuuGAUCcAsA-3' (SEQ ID 1) wherein u and c are the respective 2'-O-methyl nucleotides of the corresponding bases and s means phosphorothioate.

The RNA (2.54 μmol) equipped with a C-6 amino linker at the 5'-end was lyophilized and dissolved in 250 μL sodium borate buffer (0.1 mol/L sodium borate, pH 8.5, 0.1 mol/L KCl) and 1.1 mL DMSO. After addition of 8 μL N,N-Diisopropylethylamine (DIPEA), a solution of the GalNAc N-hydroxysuccinimid ester (theoretical 0.014 mmol) in DMF was slowly added under continuous stirring to the RNA solution. The reaction mixture was agitated at 35° C. overnight. The reaction was monitored using RP-HPLC (Resource RPC 3 ml, buffer: A: 100 mM Triethylammonium acetate (TEAA, 2.0 M, pH 7.0) in water, B: 100 mM TEAA in 95% acetonitrile, gradient: 5% B to 22% B in 20 CV). After precipitation of RNA using sodium acetate (3 M) in EtOH at −20° C., the RNA conjugate was purified using the conditions described above. The pure fractions were pooled, and the desired conjugate was precipitated using sodium acetate/EtOH to give the pure RNA conjugate. The conjugate has been isolated in 59% yield (1.50 μmol). The purity of conjugate was analyzed by anion exchange HPLC (purity: 85.5%) and identity was confirmed by ESI-MS ([M+H]$^{1+}_{calculated}$: 8374.4; [M+H]$^{1+}_{measured}$: 8376.0.

The invention claimed is:
1. A process for the preparation of a GalNAc acid derivative of the formula I:

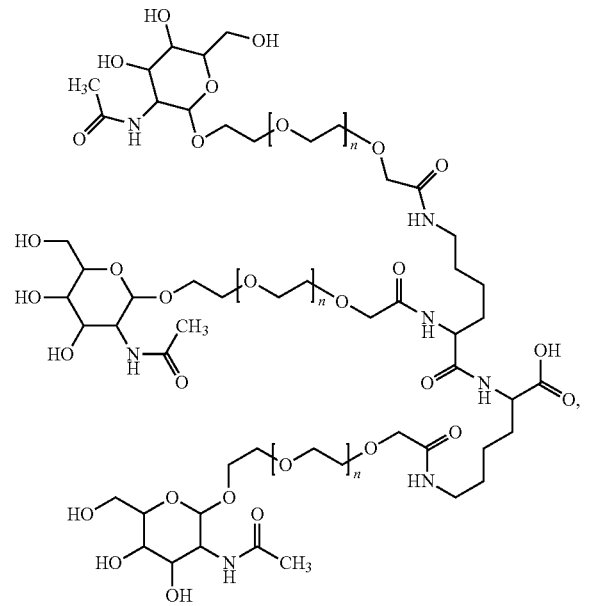

or a salt, enantiomer or optical isomer thereof, wherein n is an integer between 0 and 10, comprising the steps:
a) reacting a triamine salt of formula II:

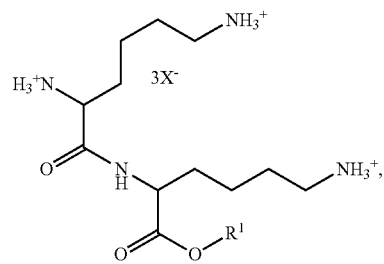

wherein $R^1$ is an ester protecting group and X is an anion of an acid, with a tetrahydropyran acid of formula III:

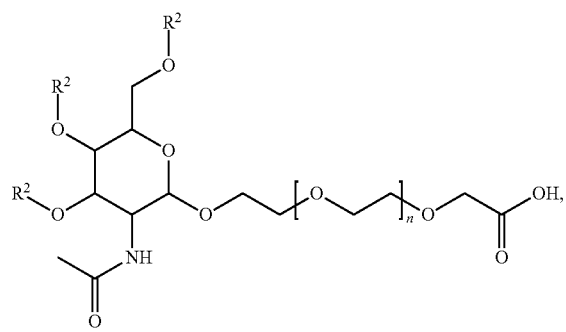

wherein $R^2$ is a hydroxy protecting group and n is as defined above, in the presence of a peptide coupling agent, an amine base and an organic solvent, to form a GalNAc ester of formula IV:

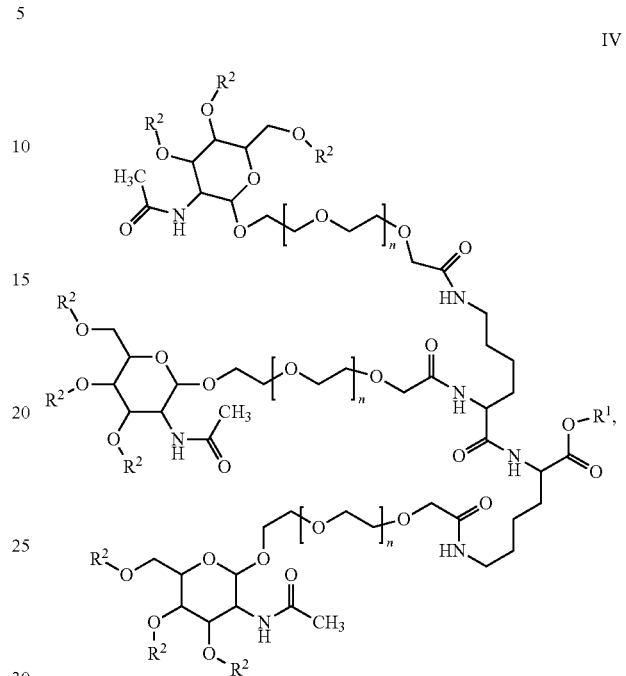

wherein $R^1$, $R^2$ and n are as defined above;
b) removing the ester protecting group $R^1$ and the hydroxy protecting groups $R^2$ in the presence of a mineral base to form a GalNAc acid salt of formula V:

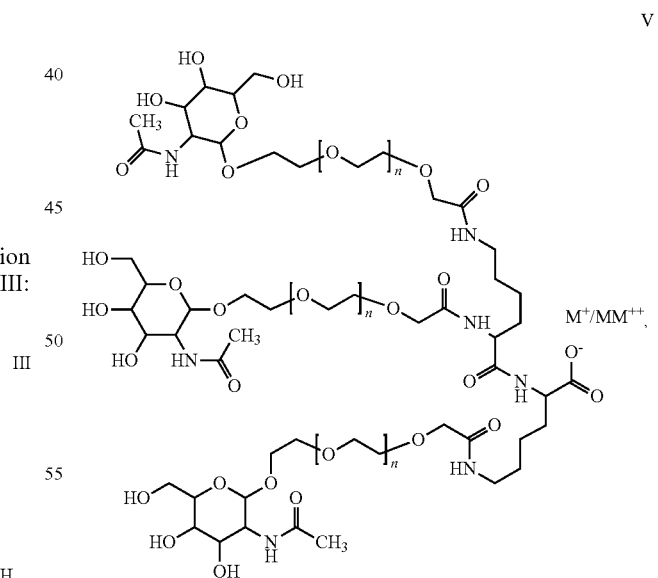

wherein n is as defined above and M is a metal cation; and
c) optionally transforming the GalNAc acid salt of formula V into the GalNAc acid derivative of formula I.

2. The process of claim 1, wherein n is an integer between 0 and 5, the ester protecting group $R^1$ is $C_{1-7}$ alkyl or phenyl-$C_{1-7}$ alkyl, wherein the phenyl group is optionally substituted with halogen or $C_{1-7}$ alkyl, the hydroxy protecting group $R^2$ is acetyl, and X is an anion of a sulfonic acid.

3. The process of claim 1, wherein the peptide coupling agent is n-propylphosphonic acid anhydride and the amine base is a tertiary amine.

4. The process of claim 1, wherein the coupling step a) takes place in an organic solvent at a reaction temperature from 20° C. to 70° C., wherein the organic solvent is a polar aprotic solvent.

5. The process of claim 1, wherein the mineral base in step b) is an alkali hydroxide.

6. The process of claim 1, wherein the steps a) and b) are combined and performed in one step without isolating the GalNAc ester of formula V.

7. The process of claim 1, wherein the optional step of transforming the GalNAc acid salt of formula V into the GalNAc acid derivative of formula I is performed via cation exchange or via treatment with an acid.

8. The process of claim 1, wherein the GalNAc acid derivative of formula I is of the formula Ia:

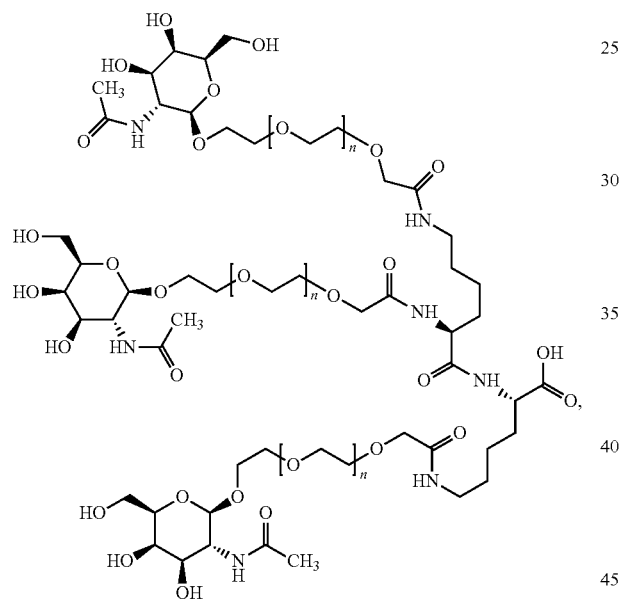

or a salt or enantiomer thereof.

9. The process of claim 1, wherein the process further comprises producing the triamine salt of formula II comprising the steps:

a1) transforming a carboxylic acid of formula X:

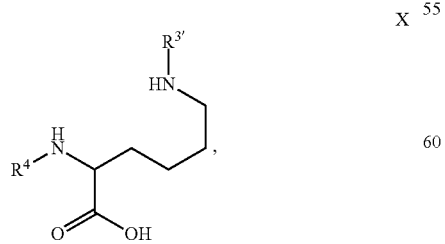

wherein R$^{3'}$ and R$^4$ are different and independently amino protecting groups, into an ester of formula XI:

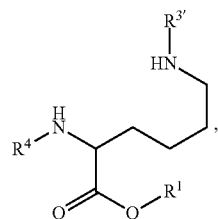

wherein R$^1$ is an ester protecting group and R$^{3'}$ and R$^4$ are as defined above;

b1) removing the amino protecting group R$^4$ in the ester of formula XI, and subsequently forming an amine salt of formula XII:

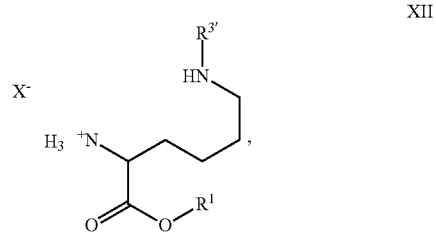

wherein R$^1$ and R$^{3'}$ are as defined above and X$^-$ is an acid anion;

c1) coupling the amine salt of formula XII with a hexanoic acid derivative of formula XIII:

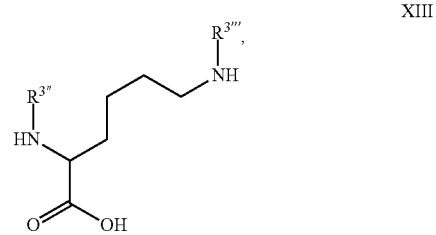

wherein R$^{3''}$ and R$^{3'''}$ are amino protecting groups to form the protected triamine of formula XIV:

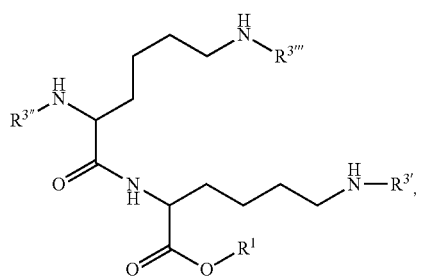

wherein R$^{3'}$, R$^{3''}$, R$^{3'''}$ and R$^1$ are as above; and d1) converting the protected triamine of formula XIV with an acid into the triamine salt of formula II.

10. Process of claim 9, wherein R$^{3'}$, R$^{3''}$ and R$^{3'''}$ are the same and protecting groups which are cleavable under acidic conditions and $R^4$ is a protecting group which is cleavable under basic conditions or by way of hydrogenolysis.

11. Process of claim 10, wherein $R^{3'}$, $R^{3'''}$ and $R^{3''''}$ are Boc and $R^4$ is FMOC.

12. Process of any one of claims 9, wherein the transformation in step a1) takes place with benzyl alcohol in the presence of an activating agent, an amine catalyst and an aprotic organic solvent at a reaction temperature of 20° C. to 50° C.

13. Process of any one of claims 9, wherein the amino protecting group $R^4$ is FMOC and its removal in step b1) is performed with a secondary aliphatic amine in a polar aprotic solvent at a reaction temperature of 20° C. to 50° C.

14. Process of any one of claims 9, wherein the subsequent formation of the amine salt of formula XII in step b1) is effected with a sulfonic acid.

15. Process of any one of claims 9, wherein the coupling in step c1) is performed with n-propylphosphonic acid anhydride as coupling agent in the presence of a tertiary amine and a polar aprotic solvent at a reaction temperature from 20° C. to 50° C.

16. The process of claim 9, wherein in step d1) the triamine salt of formula II is formed with a sulfonic acid in a polar aprotic solvent at a reaction temperature of 20° C. to 80° C.

17. The process of claim 16, wherein a polar aprotic solvent is selected which prevents the triamine salt of formula II to crystallize.

18. The process of claim 1, wherein the process further comprises producing the tetrahydropyran acid of formula III comprising the steps:

a2) transforming a diol of formula XX:

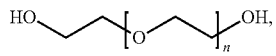

XX wherein n is as defined in claim 1, into an alcohol ester of formula XXI:

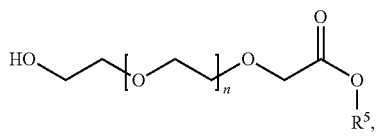

XXI wherein n is as defined in claim 1 and $R^5$ is an ester protecting group;

b2) coupling the alcohol ester of formula XXI with a tetrahydropyran derivative of formula XXII:

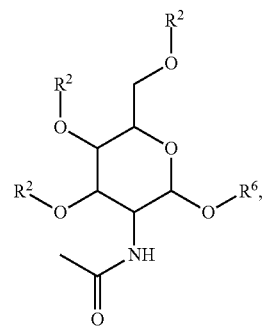

XXII wherein each $R^2$ and $R^6$ are independently hydroxy protecting groups, to form a tetrahydropyran ester of formula XXIII:

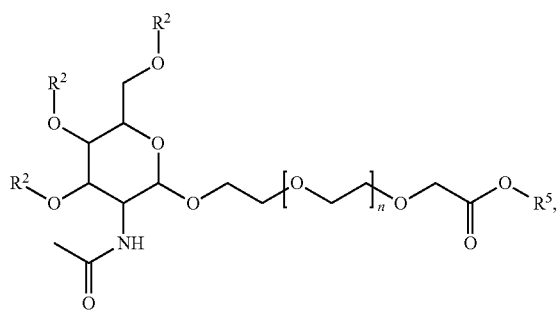

XXIII wherein n, $R^2$ and $R^5$ are as defined above; and c2) removing the ester protecting group $R^5$ to form the tetrahydropyran acid of formula III.

19. The process of claim 18, wherein the hydroxy protecting group $R^2$ is acetyl, the ester protecting group $R^5$ is benzyl and the hydroxy protecting group $R^6$ is acetyl.

20. The process of claim 18, wherein in a first step of step a2) the diol of formula XX is deprotonated with an alkali metal alcoholate in the presence of a polar protic or polar aprotic solvent at a reaction temperature from 50° C. to 120° C.

21. The process of claim 18, wherein in a second step of step a2) an acetic acid moiety is introduced with a halogen acetic acid or with a salt thereof in the presence of a polar protic or polar aprotic solvent at a reaction temperature from 50° C. to 120° C.

22. The process of claim 18, wherein in a third step of step a2) the alcohol ester of formula XXI wherein $R^5$ is benzyl is formed with a benzyl halogenide or a benzyl sulfonylester in a polar aprotic solvent at a reaction temperature from 20° C. to 120° C.

23. The process of claim 18, wherein in step b2) the alcohol ester of formula XXI is coupled with the tetrahydropyran derivative of formula XXII in the presence of a halogenated sulfonic acid in the presence of a polar aprotic solvent at a reaction temperature from 0° C. to 140° C.

24. The process of claim 18, wherein in step c2) the benzylester group is removed by a catalytic hydrogenation with hydrogen in the presence of a hydrogenation catalyst.

25. The process of claim 18, wherein the step of transforming the diol of formula XX into the alcohol ester of formula XXI comprises the steps of:

a3) reacting a 2-amino acetate of formula XXV:

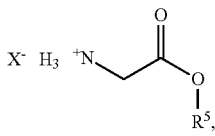

XXV wherein R⁵ is as defined in claim 18 and X is a halogen atom, with a nitrite salt to form a 2-diazo compound of formula XXVI:

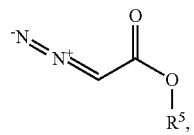

XXVI wherein R⁵ is as defined in claims 18; and b3) reacting the 2-diazo compound of formula XXVI with the diol of formula XX.

26. The process of claim 25, wherein the diazotization in step a3) is performed with an alkali nitrite in the presence of a solvent mixture of water and a non-polar aprotic solvent at a reaction temperature of −10° C. to 10° C.

27. The process of claim 25, wherein the transformation of the 2-diazo compound with the diol of formula XX in step b3) is performed in the presence of a Lewis acid and a non-polar aprotic solvent at a reaction temperature of −10° C. to 10° C.

28. A process for the preparation of a GalNAc oligonucleotide conjugate comprising the steps:

a3) preparing a GalNAc acid derivative of formula I or a GalNAc acid salt of formula V according to claim 1; and b3) conjugating the GalNAc acid derivative of formula I or the GalNAc acid salt of formula V under peptide coupling conditions with an oligonucleotide.

29. The process of claim 28, wherein the GalNAc acid salt of formula V is used.

\* \* \* \* \*